(12) United States Patent
Skulachev et al.

(10) Patent No.: US 9,572,890 B2
(45) Date of Patent: Feb. 21, 2017

(54) ORAL FORMULATIONS OF MITOCHONDRIALLY-TARGETED ANTIOXIDANTS AND THEIR PREPARATION AND USE

(71) Applicant: MITOTECH SA, Luxembourg (LU)

(72) Inventors: Maxim V. Skulachev, Moscow (RU); Vladimir P. Skulachev, Moscow (RU); Audrey A. Zamyatnin, Moscow (RU); Vadim N. Tashlitsky, Moscow (RU); Roman A. Zinovkin, Moscow (RU); Maxim V. Egorov, Troizk (RU); Lawrence T. Friedhoff, River Vale, NJ (US); Olga Y. Pletushkina, Moscow (RU); Alexander A. Andreev-Andrievsky, Moscow (RU); Tatiana V. Zinevich, Moscow (RU)

(73) Assignee: MITOTECH SA, Luxembourg (LU)

(*) Notice: Subject to any disclaimer, the term of this patent is extended or adjusted under 35 U.S.C. 154(b) by 0 days.

(21) Appl. No.: 14/887,406

(22) Filed: Oct. 20, 2015

(65) Prior Publication Data

US 2016/0038603 A1 Feb. 11, 2016

Related U.S. Application Data

(62) Division of application No. 14/123,311, filed as application No. PCT/US2012/040711 on Jun. 4, 2012, now Pat. No. 9,192,676.

(60) Provisional application No. 61/492,940, filed on Jun. 3, 2011.

(51) Int. Cl.
| | |
|---|---|
| *A61K 31/66* | (2006.01) |
| *A61K 47/48* | (2006.01) |
| *A61K 31/352* | (2006.01) |
| *A61K 31/4375* | (2006.01) |
| *C07F 9/54* | (2006.01) |
| *A61K 47/10* | (2006.01) |
| *A61K 47/12* | (2006.01) |
| *A61K 9/00* | (2006.01) |
| *A61K 47/26* | (2006.01) |
| *A61K 47/36* | (2006.01) |
| *A61K 47/14* | (2006.01) |
| *A61K 31/047* | (2006.01) |
| *A61K 31/122* | (2006.01) |

(52) U.S. Cl.
CPC ....... *A61K 47/48084* (2013.01); *A61K 9/0095* (2013.01); *A61K 31/047* (2013.01); *A61K 31/122* (2013.01); *A61K 31/352* (2013.01); *A61K 31/4375* (2013.01); *A61K 31/66* (2013.01); *A61K 47/10* (2013.01); *A61K 47/12* (2013.01); *A61K 47/14* (2013.01); *A61K 47/26* (2013.01); *A61K 47/36* (2013.01); *A61K 47/48061* (2013.01); *C07F 9/5435* (2013.01); *C07F 9/5442* (2013.01); *C07F 9/5456* (2013.01)

(58) Field of Classification Search
USPC ......................................... 514/125, 129, 453
See application file for complete search history.

(56) References Cited

U.S. PATENT DOCUMENTS

| | | | |
|---|---|---|---|
| 5,538,974 A | 7/1996 | Ogawa et al. | |
| 6,331,532 B1 | 12/2001 | Murphy et al. | |
| 7,109,189 B2 | 9/2006 | Murphy et al. | |
| 8,518,915 B2* | 8/2013 | Skulachev | A61K 31/66 |
| | | | 514/125 |
| 9,192,676 B2* | 11/2015 | Skulachev | A61K 31/352 |
| 9,233,903 B2* | 1/2016 | Skulachev | C07C 46/06 |
| 2002/0044913 A1 | 4/2002 | Hamilton | |
| 2005/0065099 A1 | 3/2005 | Walkinshaw et al. | |
| 2007/0259908 A1 | 11/2007 | Fujii et al. | |
| 2007/0270381 A1 | 11/2007 | Murphy et al. | |
| 2008/0176929 A1 | 7/2008 | Skulachev | |
| 2008/0275005 A1 | 11/2008 | Murphy et al. | |
| 2010/0234326 A1 | 9/2010 | Skulachev et al. | |
| 2010/0273892 A1 | 10/2010 | Miller et al. | |
| 2010/0292625 A1* | 11/2010 | Skulachev | A61K 8/55 |
| | | | 602/50 |
| 2010/0323992 A1 | 12/2010 | Skulachev et al. | |
| 2011/0053895 A1 | 3/2011 | Skulachev et al. | |
| 2011/0077159 A1 | 3/2011 | Skulachev et al. | |

FOREIGN PATENT DOCUMENTS

| | | |
|---|---|---|
| EP | 1047701 B1 | 5/2005 |
| EP | 1534720 A1 | 6/2005 |
| EP | 1321138 B1 | 4/2006 |
| WO | 99/26582 A2 | 6/1999 |
| WO | 2004/014927 A1 | 2/2004 |
| WO | 2006/005759 A2 | 1/2006 |
| WO | 2007/046729 A1 | 4/2007 |
| WO | 2008/048134 A1 | 4/2008 |
| WO | 2009/005386 A1 | 1/2009 |
| WO | 2009/158348 A1 | 12/2009 |

OTHER PUBLICATIONS

Nakanishi et al. CAS: 133: 213845, 2000.*
Antonenko et al. CAS: 149: 261445, 2008.*
Karalezli et al. (2011) "Homocysteine and Serum-Lipid Levels in Pulmonary Embolism," Clin. Appl. Thromb. Hemost., Epub ahead of print.
Karl et al. (2003) "Behavioral phenotyping of mice in pharmacological and toxicological research," Exp. Toxicol. Pathol., 55(1):69-83.
Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005 : 1-18, Invest. Ophthalmol. Vis. Sci., 46(9):3426-3434.

(Continued)

Primary Examiner — Rei-Tsang Shiao
(74) Attorney, Agent, or Firm — Ann-Louise Kerner; DLA Piper LLP (US)

(57) ABSTRACT

Provided are stable liquid and solid formulations of oxidized and reduced mitochondria-targeted antioxidants, and methods of their preparation and use.

9 Claims, 10 Drawing Sheets

(56) References Cited

OTHER PUBLICATIONS

Kirkinezos et al (2001) "Reactive Oxygen species and Mitochondrial Diseases," Seminars in Cell & Developmental Biology, 12:449-457.
Kirste et al. (1995) "Continuous-wave electron spin resonance studies of porphyrin and porphyrin-quinone triplet states," J. Chem. Soc. Perkin Trans. 2:2147-2152.
Kolling et al. (2011) "Homocysteine induces oxidative-nitrative stress in heart of rats: prevention by folic acid," Cardiovasc. Toxicol., 11:67-73.
Kroemer et al. (1995). The biochemistry of programmed cell death. Faseb J 9, 1277-1287.
Kromhout (2001) "Diet and cardiovascular diseases," J. Nutr. Health Aging, 5:144-149.
Kurreck et al. (1995) "Mimicking primary processes in photosynthesis covalently linked porphyrin quinones," Radiation Physics and Chemistry, 45(6):853-865.
Kutala et al. (2006) "Prevention of postischemic myocardial reperfusion injury by the combined treatment of NCX-4016 and Tempol." J. Cardiovasc. Pharmacol., 48(3):79-87.
Li et al. (2002). Activation of macrophage nuclear factor-kappa B and induction of inducible nitric oxide synthase by LPS. Respir Res 3, 23 (6 pages).
Liu et al. (1996). Induction of apoptotic program in cell-free extracts: requirement for dATP and cytochrome c. Cell 86, 147-157.
Lott et al. (2011) "Down syndrome and dementia: A randomized, controlled trial of antioxidant supplementation," Am. J. Med. Genet. A, 155:1939-1948.
Lloret et al. (2011) "Alzheimer's amyloid-β toxicity and tau hyperphosphorylation are linked via RCAN1," J. Alzheimers Dis., 27(4):701-709.
Lysenko et al. (2001) "Thrombocytopathies and their role in the development of hemorrhagic syndrome in vascular diseases of the fundus oculi," Vestn. Oftalmol., 117(1):24-26 (English Translation of Russian article abstract—1 page).
Maire et al. (2001) "Factors associated with hyperhomocysteinemia in Crohn's disease," Gastroenterol. Clin. Biol., 25 (8-9):745-748 (French-abstract only, 1 page).
Makhro et al. (2008) "Prenatal Hyperhomocysteinemia as a Model of Oxidative Stress of the Brain," Bull. Exper. Biol. & Med., 146(1):33-35.
Malenka et al. (1999) "Long-term potentiation: a decade of progress?" Science, 285(5435):1870-1874.
Matsumoto et al. (1992). Antioxidant effect on renal scarring following infection of mannose-sensitive-piliated bacteria. Nephron 60, 210-215.
Monaco et al. (2004) "Canonical pathway of nuclear factor κB activation selectively regulates proinflammatory and prothrombotic responses in human atherosclerosis," PNAS, 101(15):5634-5639.
Molloy et al. (2009) "Maternal vitamin B12 status and risk of neural tube defects in a population with high neural tube defect prevalence and no folic Acid fortification," Pediatrics, 123:917-923.
Morandi et al. (2011). A mixture of bacterial mechanical lysates is more efficient than single strain lysate and of bacterial-derived soluble products for the induction of an activating phenotype in human dendritic cells. Immunol Lett 138, 86-91.
Mundi et al. (1991). Extracellular release of reactive oxygen species from human neutrophils upon interaction with *Escherichia coli* strains causing renal scarring. Infect Immun 59,4168-4172.
Murphy (1997) "Selective Targeting of Bioactive Compounds to Mitochondria," Trends in Biotechnology, 15 (8):326-330.
Murphy et al. (2007) Targeting antioxidants to mitochondria by conjugation to lipophilic cations. Annu. Rev. Pharmacol. Toxicol., 47:629-656.
Murphy et al. (2011) "Homocysteine in pregnancy," Adv. Clin. Chem., 53:105-37.
Oddo et al. (2003) "Triple-transgenic model of Alzheimer's disease with plaques and tangles: intracellular Abeta and synaptic dysfunction," Neuron, 39:409-421.
O'Hanley et al. (1996). Prospects for urinary tract infection vaccines. In: Urinary Tract Infections: Molecular Pathogenesis and Clinical Management (Mobley, H. L. T. & Warren, J.W., eds), (Washington, DC: ASM Press), pp. 405-425 (23 pages).
O'Hanley et al. (1991). Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis. Infect Immun 59, 1153-1161.
Okada et al. (2005) "The implications of the upregulation of ICAM-1/VCAM-1 expression of corneal fibroblasts on the pathogenesis of allergic keratopathy," Invest. Ophthalmol. Vis. Sci., 46(12):4512-4518.
Pagani et al. (2011) "Amyloid-Beta interaction with mitochondria." Int. J. Alzheimer's Dis., Art. 925050 (12 pages).
Parascandola (1974) "Dinitrophenol and bioenergetics: an historical perspective," Mol. Cell. Biochem., 5(1-2):69-77.
Petit-Demouliere et al. (2005) "Forced swimming test in mice: a review of antidepressant activity," Psychopharmacol., 177:245-255.
Plotnikov et al. (2008) "Interrelations of Mitochondrial Fragmentation and Cell Death Under Ischemia/Reoxygenation and UV-Irradiation: Protective Effects of SkQ1, Lithium Ions and Insulin," FEBS Letters, 582:3117-3124.
Plotnikov et al. (2010) "New-generation Skulachev ions exhibiting nephroprotective and neuroprotective properties." Biochemistry (Mosc.), 75(2):145-150.
Poehlman et al. (1989) "A review: exercise and its influence on resting energy metabolism in man," Med. Sci. Sports Exerc., 21(4):515-525.
Rodriguez-Spong et al. (2004) "General Principles of Pharmaceutical Solid Polymorphism: A Supramolecular Perspective," Advanced Drug Delivery Reviews, 56:241-274.
Rogers (2008) "Has enhanced folate status during pregnancy altered natural selection and possibly Autism prevalence? a closer look at a possible link," Med. Hypoth., 71:406-410.
Saifer et al. (1957) "Laboratory Methods: The photometric microdetermination of blood glucose with glucose oxidase," J. Lab. Clin. Med., 51(3):448-460.
Sakaguchi et al. (2007). "Preventive effects of a biscoclaurine alkaloid, cepharanthine, on endotoxin or tumor necrosis factor-alpha-induced septic shock symptoms: involvement of from cell death in L929 cells and nitric oxide production in raw 264.7 cells," Int. Immunopharmacol. 7:191-197.
Sanmun et al. (2009) "Involvement of a functional NADPH oxidase in neutrophils and macrophages during programmed cell clearance: implications for chronic granulomatous disease," Am. J. Physiol. Cell Physiol. 297: C621-631.
Sarter (2002) Coenzyme Q10 and Cardiovascular Disease: A Review, J. Cardiovasc. Nurs. 16(4):9-20.
Selkoe (2002) "Alzheimer's disease is a synaptic failure," Science 298:789-791.
Smith et al. (2008) "Mitochondria-targeted antioxidants in the treatment of disease,"Ann. N.Y. Acad. Sci., 1147:105-111.
Silachev et al. (2011) "New generation of permeated cations as potential agents to rescue from ischemic stroke," FEBS J., 278(1):280 (Russian — abstract only, 1 page).
Skulachev (2005) "Critical Review: How to Clean the Dirtiest Place in the Cell: Cationic Antioxidants as Intramitochondrial ROS Scavengers," IUBMB Life, 57(4/5):305-310.
Skulachev et al. (2005) "Aging as mitochondria-mediated atavistic program. Can aging be switched off?" Ann. N.Y. Acad. Sci., 1057:145-164.
Skulachev et al. (2009) "An attempt to prevent senescence: a mitochondrial approach," Biochimica et Biophysica Acta., 1787:437-461.
Smith, et al. (2003) "Delivery of bioactive molecules to mitochondria in vivo," PNAS, 100(9):5407-5412.
Snow et al. (2010) "A double-blind, placebo-controlled study to assess the mitochondria-targeted antioxidant MitoQ as a disease-modifying therapy in Parkinson's disease," Mov. Disord. 25(11):1670-1674.
Spector (1995) "Oxidative stress-induced cataract: mechanism of action," FASEB J., 9:1173-1182.

(56) References Cited

OTHER PUBLICATIONS

Spencer et al. (1998) "Transition metal chelators reduce directly measured myocardial free radical production during reperfusion," J. Cardiovasc. Pharmacol., 32(3):343-348.
Stefanova et al. (2010) "Behavioral effects induced by mitochondria-targeted antioxidant SkQ1 in Wistar and senescence-accelerated OXYS rats," J. Alzheimer's Dis. 21:479-491.
Stella et al. (2007) Prodrugs: Challenges and Rewards, Springer, New York Part 1 and 2 (17 pages).
Tauskela (2007) "MitoQ—a mitochondria-targeted antioxidant," IDrugs, 10:399-412.
Triet et al. (1993) "Anxiogenic stimuli in the elevated plus-maze," Pharmacol. Biochem. & Behav. 44:463-469.
USDH (2005) Guidance for Industry: Estimating the Maximum Safe Starting Dose in Initial Clinical Trials for Therapeutics in Adult Healthy Volunteers, U.S. Dept. of Health and Human Services, FDA, CDER (30 pages).
Vanden Hoek et al. (1996) "Reperfusion injury in cardiac myocytes after simulated ischemia," Am. J. Phys., 270:1334-1341.
Venuraju et al. (2010) "Osteoprotegerin as a Predictor of Coronary Artery Disease and Cardiovascular Mortality and Morbidity,"J. Am. Coll. Cardiol. 55(19):2049-2061.
Viana et al. (2004) "Hypoglycemic and anti-lipemic effects of the aqueous extract from Cissus sicyoides," BMC Pharmacol. 4:9 (7 pages).
Vlachantoni et al. (2011) "Evidence of severe mitochondrial oxidative stress and a protective effect of low oxygen in mouse models of inherited photoreceptor degeneration," Human Mol. Gen. 20(2):322-335.
Villa et al. (2004) "Animal models of endotoxic shock" Meth. Mol. Med., 98:199-206.
Vollset et al. (2000) "Plasma total homocysteine, pregnancy complications, and adverse pregnancy outcomes: the Hordaland Homocysteine study," Am. J. Clin. Nutr., 71:962-968.
Weyer et al. (1999) "Development of beta3-adrenoceptor agonists for the treatment of obesity and diabetes—an update," Diabetes Metab., 25:11-21.
Xu et al. (2011) "Methionine diet-induced hyperhomocysteinemia accelerates cerebral aneurysm formation in rats," Neurosci. Lett., 494(2):139-44.
Zamzami et al. (1996), "Mitochondrial control of nuclear apoptosis," J. Exp. Med. 183:1533-1544.
Zoratti et al. (1995), "The mitochondrial permeability transition," Biochim. Biophys. Acta. 1241:139-176.
Zettl et al. (2005) "Investigation of micelle formation by fluorescence correlation spectroscopy," J. Phys. Chem. B. 109:13397-13401.
Zorov et al. (2000), "Reactive oxygen species (ROS)-induced ROS release: a new phenomenon accompanying induction of the mitochondrial permeability transition in cardiac myocytes," J. Exp. Med. 192:1001-1014.
Zorov et al. (2006), "Mitochondrial ROS-induced ROS release: an update and review," Biochim. Biophys. Acta. 1757:509-517.
International Search Report and Written Opinion of the International Searching Authority, PCT/US12/40711, Aug. 20, 2012 (9 pages).
Hobbs et al., Neonatal rat hypoxia-ischemia: effect of the antioxidant mitoquinol, and s-PBN, CAS: 150: 345197, 2008.
Skulachev et al., Pharmaceutical substances of mitochondria-targeted antioxidants containing a quinone fragment linked with a Skulachev-type ion, or amphiphilic fragment, through a hydrocarbon or isoprenoid chain, CAS: 154: 615390, 2011.
Anisimov et al. (2008) Mitochondria-Targeted Plastoquinone Derivatives as Tools to Interrupt Execution of the Aging Program. 5. SkQ1 Prolongs Lifespan and Prevents Development of Traits of Senescence, Biochemistry (Moscow) 73 (12):1329-1342.
Shipounova et al. (2010) Reactive oxygen species produced in mitochondria are involved in age-dependent changes of hematopoietic and mesenchymal progenitor cells in mice. A study with the novel mitochondria-targeted antioxidant SkQ1, Mechanisms of Aging and Development, 131(6):415-421.
James et al., Interactions of Mitochondria-targeted and Untargeted Ubiquinones with the mitochondrial respiratory chain and reactive oxygen species: implications for the use of exogenous ubiquinones as therapies and experimental tools, CAS: 143:148390, 2005.
Liu, Antitumor sustained-release injection containing taxane and its synergistic agent, CAS: 145:495544, 2006.
Adlam et al. (2005) "Targeting an antioxidant to mitochondria decreases cardiac ischemia-reperfusion injury," FASEB J., 19:1088-1095.
Anisimov (2007) "Molecular and Physiological Mechanisms of Aging," Antioksidanty, Nov. 27, 2007, [on line] http://imquest.alfaspace.net/BOOK/MFMA/mfma_3_9_2.htm?embedded=yes translated from Russian to English.
Antonenko et al. (2008) "Protective effects of mitochondria-targeted antioxidant SkQ in aqueous and lipid membrane environments," J. Membr. Biol., 222:141-149.
Becker (2004) "New concepts in reactive oxygen species and cardiovascular reperfusion physiology" Cardiovascular Research, 61:461-470.
Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep, 26:231-243.
Brand et al. (1992) "The mechanism of the increase in mitochondrial proton permeability induced by thyroid hormones," Eur. J. Biochem. 206:775-781.
Doughan et al. (2007) "Original Research Communication: Mitochondrial Redox Cycling of Mitoquinone Leads to superoxide Production and Cellular Apoptosis," Antioxid. & Redox Signal., 9(11):1825-1836.
Faloon et al. Preparation of Substituted Aminonaphthalenediones as Inhibitors of the MITF molecular Pathway, CAS: 162: 92534,2014.
Green et al. (2004) "Prevention of Mitochondrial Oxidative Damage as a Therapeutic Strategy in Diabetes," Diabetes, 53(1):S110-S118.
Hansford et al. (1997) "Dependence of H2O2 formation by rat heart mitochondria on substrate availability and donor age," J. Bioenerg. Biomem. 29(1):89-95.
Holloszy (1998) "Longevity of exercising male rats: effect of an antioxidant supplemented diet," Mechanisms of Ageing and Development, 100:211-219.
King et al. (2004) "Mitochondria-derived reactive oxygen species mediate blue light-induced death of retinal pigment epithelial cells," Photochem. and Photobiol, 79(5):470-475.
Kirschner et al. (1994) "Role of iron and oxygen-derived free radicals in ischemia-reperfusion injury" J. Am. Coll. Surg., 179:103-117.
Li et al. (2000) "Skeletal muscle respiratory uncoupling prevents diet-induced obesity and insulin resistance in mice," Nat. Med. 6(10):1115-1120.
Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.
Longo et al. (2005) "Programmed and altruistic ageing," Nature Reviews Genetics, 6:866-872.
Lou et al. (2007) "Mitochondrial Uncouplers With an Extraordinary Dynamic Range," Biochem. J., 407:129-140.
Mecocci et al. (2000) "Plasma antioxidants and longevity: a study on healthy centenarians," Free Radical Biology and Medicine, 28(8):1243-1248.
Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73 (12):1317-1328.
Orr et al. (2003) "Effects of overexpression of copper-zinc and manganese superoxide dismutases, catalase, and thioredoxin reductase genes on longevity in *Drosophila melanogaster*," J. Biol. Chem., 278(29):26418-26422.

(56) References Cited

OTHER PUBLICATIONS

Papp et al. (1999) "Glutathione status in retinopathy of prematurity," Free Radic. Biol. & Med., 27(7-8):738-743.
Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.
Petrosillo et al. (2006) "Protective effect of melatonin against mitochondrial dysfunction associated with cardiac ischemia-reperfusion: role of cardiolipin," FASEB J., 20:269-276.
Popova et al. (2006) "MitoQ induced miofibroblast differentiation of human fibroblasts," Biochimica et Biophysica Acta, P2.2. 27:S:433-434.
Pozniakovsky et al. (2005) "Role of mitochondria in the pheromone- and amiodarone-induced programmed death of yeast, " J. Cell Biol., 168(2):257-69.
Reddy (2006) "Mitochondrial oxidative damage in aging and Alzheimer's disease: implications for mitochondrially targeted antioxidant therapeutics," J. Biomedicine and Biotech., Art.ID 31372:1-13.
Reliene et al. (2007) "Antioxidants suppress lymphoma and increase longevity in the atm-deficient mice," J. Nutrition, 37:229S-232S.
Riess et al. (2004) "Reduced reactive O2 species formation and preserved mitochondrial NADH and [Ca2+] levels during short-term 17° C. ischemia in intact hearts," Cardiovascular Research, 61:580-590.
Skulachev (2007) "A Biochemical Approach to the Problem of Aging: 'Megaproject' on Membrane-Penetrating Ions. The First Results and Prospects," Biochem. (Moscow), 72(12):1385-1396.
Sheu et al. (2006) "Targeting antioxidants to mitochondria: a new therapeutic direction," Biochimica et Biophysica Acta, 1762:256-265.
Sidorova et al. (2004) "Transcriptional activation of cytochrome P450 1A1 with alpha-tocopherol," Bull Exp. Bio. Med., 138(3):233-236.
Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.
Starkov et al. (1997) "6-ketocholestanol is a recoupler for mitochondria, chromatophores and cytochrome oxidase proteoliposomes," Biochim. Biophys. Acta. 1318:159-172.
Tompkins et al. (2006) "Mitochondrial dysfunction in cardiac ischemia-reperfusion injury: ROS from complex I, without inhibition," Biochim Biophys Acta 1762:223-231.
Yildirim et al. (2005) "Role of oxidative stress enzymes in open-angle glaucoma," Eye, 19:580-583.
Zweier et al. (1987) "Direct measurement of free radical generation following reperfusion of ischemic myocardium," PNAS USA, 84:1404-1407.
International Search Report dated Dec. 20, 2007 and International Preliminary Report on Patentability dated Nov. 10, 2009, PCT/RU2007/000171 (16 pages).
International Search Report and Written Opinion of the International Searching Authority, PCT/RU2007/000355, Mar. 27, 2008, 10 pages.
PCT International Preliminary Report on Patentability for International Application No. PCT/RU2007/000043, issued Aug. 4, 2009, 7 pages.
PCT International Search Report for PCT Application No. PCT/RU2007/000043, mailed Nov. 1, 2007, 2 pages.
PCT International Search Report and Written Opinion of the International Searching Authority for PCT Application No. PCT/RU2006/000546, mailed Jul. 5, 2007, 14 pages.
International Search Report, PCT/RU2008/000706, Aug. 13, 2009 (3 pages).
International Search Report and Written Opinion of the International Searching Authority, PCT/RU2009/000295, Feb. 25, 2010, 7 pages.
International Search Report and Written Opinion, PCT/RU2009/000621, dated Aug. 12, 2010 (12 pages).
International Search Report and Written Opinion, PCT/RU2006/000394, dated Nov. 2, 2006 (6 pages).
International Search Report and Written Opinion, PCT/RU2006/000547, dated Jul. 5, 2007 (7 pages).
International Search Report and Written Opinion, PCT/RU2007/000044, dated Nov. 1, 2007 (9 pages).
Shchepinov et al., Disorders Implicating PUFA Oxidation, CAS: 157: 681581, 2012.
Agapova, et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).
Antonenko, et al. (2008) "Mitochondria-Targeted Plastoquinone Derivatives as Tools to Interrupt Execution of the Aging Program. 1. Cationic Plastoquinone Derivatives: Synthesis and in Vitro Studies," Biochem. (Mosc)., 73 (12):1273-1287 (+ 1 fig. page).
Dugina, et al. (2009) "β- and γ-Cyoplasmic Actins Display Distinct Distribution and Functional Diversity," J. Cell Sci., 122(16):2980-2988.
Fernández-Medarde, et al. (2011) "Ras in Cancer and Developmental Diseases," Genes & Canc., 2(3):344-358.
Havens, et al. (2006) "Regulation of Late G1/S Phase Transition and APCCdh1 by Reactive Oxygen Species," Mol. Cell. Biol., 26(12):4701-4711.
Popova, et al., (2010) "Scavenging of Reactive Oxygen Species in Mitochondria Induces Myofibroblast Differentiation," Antiox. & Redox. Signal., 13(9):1297-1307.
Sundaresan, et al. (1995) "Requirement for Generation of H2O2 for Platelet-Derived Growth Factor Signal Transduction," Science, 270:296-299.
13-Methoxydihydronitidine—Compound Summary PubChem compound CID 38845; Mar. 26, 2005 (Mar. 26, 2005) [retrieved_from http://pubchem.ncbi.nlm.nih.gov/summary/summary.cgi?cid=38845&loc=ec_rcs on Jul. 31, 2012] whole doc (4 pages).
Andrades, et al. (2011) "Bench-to-bedside review: sepsis—from the redox point of view," Crit. Care 15:230.
Astrup et al. (1996) "Low resting metabolic rate in subjects predisposed to obesity: a role for thyroid status 1-3," Am. J. Clin. Nutr. 63:879-883.
Azizi et al. (2010) "Effects of hyperhomocysteinemia during the gestational period on ossification in rat embryo," Bone, 46:1344-1348.
Bacsi et al. (2005) "Effect of pollen-mediated oxidative stress on immediate hypersensitivity reactions and late-phase inflammation in allergic conjunctivitis," J. Allergy Clin. Immunol., 116(4): 836-843.
Bakeeva et al. (2008) "Mitochondria-targeted plastoquinone derivatives as tools to interrupt execution of the aging program. 2. Treatment of some ROS- and Age-related diseases (heart arrhythmia, heart infarctions, kidney ischemia, and stroke)," Biochemistry (Moscow), 73(12):1288-1299 and 1 figure.
Barclay et al. (2003) Phenols as antioxidants. In the Chemistry of Phenols, Part 2, Rappoport, Z., Ed., Wiley, pp. 875 (3 pages).
Bernard et al. (2002) "Hytopthermia after cardiac arrest study group. Mild therapeutic hypothermia to improve the neurologic outcome after cardiac arrest," New Engl. J. Med. 346(8):549-556.
Bhate et al. (2008) "Vitamin B12 status of pregnant Indian women and cognitive function in their 9-year-old children," Food Nutr. Bull., 29:249-54.
Bravo et al. (2011) "High fat diet-induced non alcoholic fatty liver disease in rats is associated with hyperhomocysteinemia caused by down regulation of the transsulphuration pathway," Lipids Health Dis., 10:60.
Bray et al. 1999) "Sibutramine produces dose-related weight loss," Obes. Res. 7(2):189-198.
Byrom (1933) "Nature of myxoedema," Clin. Sci. 1:273-285.
Cherubini et al. (2005). Potential markers of oxidative stress in stroke. Free Radic Biol Med 39,841-852.

(56) References Cited

OTHER PUBLICATIONS

Clapham et al. (2000) "Mice overexpressing human uncoupling protein-3 in skeletal muscle are hyperphagic and lean," Nature, 406:415-418.
Clem et al. (2008) "Small-molecule inhibition of 6-phosphofructo-2-kinase activity suppresses glycolytic flux and tumor growth," Mol. Canc. Ther. 7(1):110-120.
Collins et al. (2004) "Heart protection study collaborative group. Effects of cholesterol-lowering with simvastatin on stroke and other major vascular events in 20536 people with cerebrovascular disease or other high-risk conditions," Lancet 363(9411):757-767.
Coulter et al. (2000) "Mitochondrially targeted antioxidants and thiol reagents," Free Rad. Biol. Med. 28 (10):1547-1554.
Demougeot et al. (2004) "Cytoprotective efficacy and mechanisms of the liposoluble iron chelator 2,2'-dipyridyl in the rat photothrombotic ischemic stroke model," J. Pharmacol. Exper. Ther. 311:1080-1087.
Denisov (2006) "Reactivity of quinones as alkyl radical acceptors," Kinetics and Catalysis, 45(5):662-671.
Deshmukh et al. (2010) "Effect of physiological doses of oral vitamin B12 on plasma homocysteine: a randomized, placebo controlled, double-blind trial in India," Eur. J. Clin. Nutr., 64: 495-502.
Dominguez (2006), "Ageing, lifestyle modifications, and cardiovascular disease in developing countries," J. Nutr. Health Aging, 10(2):143-149.
Faa et al. (1999) "Iron chelating agents in clinical practice," Coordination Chemistry Reviews, 184(1):291-310.
Galkina et al. (2004). Endothelium-leukocyte interactions under the influence of the superoxide-nitrogen monoxide system. Med Sci Monit 10, BR307-316.
Ge et al. (2010) "Cardiac-Specific Overexpression of Catalase Attenuates Paraquat-Induced Myocardial Geometric and Contractile Alteration: Role of ER Stress," Free Rad. Biol. & Med., 49(12):2068-2077.
Green (1974) "The electromechanochemical model for energy coupling in mitochondria," Biochimica et Biophysica Acta, 346:27-78.
Gear (1974) "Rhodamine 6G: A potent inhibitor of mitochondrial oxidative phosphorylation," J. Biol. Chem., 249 (11):3628-3637.
Giamarellos-Bourboulis et al. (2006). Oleuropein: a novel immunomodulator conferring prolonged survival in experimental sepsis by Pseudomonas aeruginosa. Shock 26(14), 410-416.
Giorgini et al. (2001) "Reactivity of ubiquinones and ubiquinols with free radicals." Free Rad. Res. 35:63-72.
Goldstein (2002) "Reactive oxygen species as essential components of ambient air," Biochemistry (Mosc.) 67:161-170.
Gong et al. (1997) "Uncoupling protein-3 is a mediator of thermogenesis regulated by thyroid hormone, beta3- adrenergic agonists, and leptin," J. Biol. Chem., 272(39):24129-24132.
Gorgone et al (2009) "Hyperhomocysteinemia in patients with epilepsy: does it play a role in the pathogenesis of brain atrophy? A preliminary report," Epilepsia, 50(1):33-36.
Griffiths et al. (2001) "Genetic analysis of collagen-induced arthritis in rats: a polygenic model for rheumatoid arthritis predicts a common framework of cross-species inflammatory/autoimmune disease loci." Immunol. Rev. 184:172-83.
Haass et al. (2007) "Soluble protein oligomers in neurodegeneration: lessons from the Alzheimer's amyloid beta-peptide." Nat. Rev. Mol. Cell. Biol. 8:101-112.
Honzik et al. (2010) "Clinical presentation and metabolic consequences in 40 breastfed infants with nutritional vitamin B12 deficiency—what have we learned?" J. Paediatr. Neurol., 14:488-95.
Herrmann et al. (2011) "Homocysteine: a biomarker in neurodegenerative diseases," Clin. Chem. Lab. Med., 49:435-41.
Hess et al. (2002) "Biological and Chemical Applications of Fluorescence Correlation Spectroscopy: A Review," Biochem. 41(3):697-705.
Hummel et al. (1966) "Diabetes, new mutation in the mouse." Science, 153:1127-1128.
Hunter et al. (1979). The Ca2+-induced membrane transition in mitochondria. I. The protective mechanisms. Arch Biochem Biophys 195, 453-459.
Hvizdos et al. (1999) "Orlistat: a review of its use in the management of obesity," Drugs, 58(4):743-760.
Johnson et al. (1980) "Localization of Mitochondria in Living Cells with Rhodamine 123," Proc. Natl. Acad. Sci. USA, 77(2):990-994.
Jolkkonen (2000) "Behavioral effects of the alpha(2)-adrenoceptor antagonist, atipamezole, after focal cerebral ischemia in rats," Eur. J. Pharmacol., 400, 211-219.
Juhaszova et al. (2004). Glycogen synthase kinase-3beta mediates convergence of protection signaling to inhibit the mitochondrial permeability transition pore. J Clin Invest 113, 1535-1549.

\* cited by examiner

ORAL FORMULATIONS OF MITOCHONDRIALLY-TARGETED ANTIOXIDANTS AND THEIR PREPARATION AND USE

CROSS-REFERENCE TO RELATED APPLICATION

This application is a division of U.S. application Ser. No. 14/123,311, entitled "Oral Formulations of Mitochondrially-Targeted Antioxidants and Their Preparation and Use," filed on Dec. 2, 2013, which is the national phase under 35 U.S.C. §371 of International Application No. PCT/US2012/040711, entitled "Oral Formulations of Mitochondrially-Targeted Antioxidants and Their Preparation and Use," filed on Jun. 4, 2012, which claims priority to and the benefit of U.S. Provisional Patent application Ser. No. 61/492,940 entitled "Oral Formulations of Mitochondrially-Targeted Antioxidants and Their Medical Use" which was filed Jun. 3, 2011. The entirety of the aforementioned applications are herein incorporated by reference.

FIELD OF THE INVENTION

This disclosure is in the fields of cell biology, pharmacology and medicine, and in particular, inflammation, diabetes, septic shock, wound healing, and coronary heart disease.

BACKGROUND

Promising therapeutical properties of mitochondria-targeted antioxidants (MTAs) have been described (see, e.g., US2008176929; Skulachev et al. (2009), *Biochim. Biophys. Acta,* 1787:437-61). The experiments performed which revealed these properties were done with freshly prepared solutions of MTAs and made by dissolving of ethanol stock solutions preserved at −80° C. shortly before administration of the preparation to animals. Such method of preparation and administration is not suitable or realistic for preparation of pharma-ceuticals as it is extremely inconvenient if not impossible for industrial manufacturing, logistics, and use by patients. Attempts to develop a pharmaceutical composition (for oral administration or injection) with acceptable stability revealed that MTAs are not stable in most types of oral or injectable compositions. Stable pharmaceutical composition containing MTAs possessing acceptable stability have not been described up to now. Accordingly, improved liquid formulations with stability are still needed.

SUMMARY

The present disclosure provides stabilized liquid and solid formulations comprising MTAs suitable for oral, nasal, and intravenous and injectable administration, and methods of preparation of such formulations. The invention also provides methods of treatment and prophylaxis of diseases and conditions relating to mitochondria using such formulations.

In one aspect, the disclosure provides a stabilized pharmaceutical formulation comprising a compound of Formula I in oxidized and/or reduced form.

The compound of Formula I is:

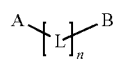

(I)

wherein:
A is an antioxidant of Formula II:

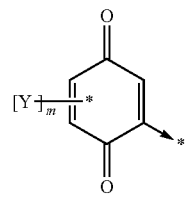

(II)

and/or reduced form thereof, wherein m comprises an integer from 1 to 3;
Y is independently selected from the group consisting of: lower alkyl, lower alkoxy, or two adjacent Y groups, together with carbon atoms to which they are attached, form a following structure of Formula III:

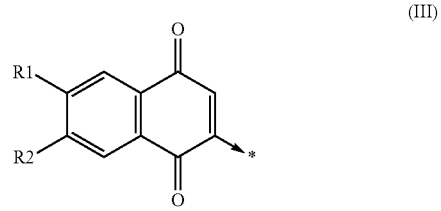

(III)

and/or reduced form thereof, wherein:
R1 and R2 are the same or different and are each independently lower alkyl or lower alkoxy;
L is a linker group, comprising: a) a straight or branched hydrocarbon chain optionally substituted by one or more double or triple bond, or ether bond, or ester bond, or C—S, or S—S, or peptide bond; and which is optionally substituted by one or more substituents preferably selected from alkyl, alkoxy, halogen, keto group, amino group; or b) a natural isoprene chain;
n is an integer from 1 to 20; and
B is a targeting group comprising: a) a Skulachev-ion Sk ($Sk^+$ $Z^-$) wherein: Sk is a lipophillic cation or a lipophillic metalloporphyrin, and Z is a pharmaceutically acceptable anion; or b) an amphiphillic zwitterion,
with the proviso that in compound of Formula I, A is not ubiquinone (e.g., 2-methyl-4,5-dimethoxy-3,6-dioxo-1,4-cyclohexadienyl) or tocopherol or a mimetic of superoxide dismutase or ebselen; when L is divalent decyl, divalent pentyl, or divalent propyl radical; and when B is triphenylphosphonium cation.

In a particular embodiment, the composition is reduced or is oxidized. In some embodiments, the formulation is in liquid form, and in other embodiments, the formulation is in solid form.

In some embodiments the liquid formulation comprises a compound of Formula I in 10% to 100% glycerol, from about 10% to about 100% glycol, (e.g., 1,2-propylene glycol) or from about 1% to about 100% (absolute) ethanol. In one particular embodiment, the composition of Formula I is in about 50% 1,2-propylene glycol.

The disclosure also provides stabilized solid pharmaceutical formulations comprising a compound of Formula I in oxidized or reduced form, with the proviso that in compound of Formula I, A is not ubiquinone (e.g., 2-methyl-4,5-dimethoxy-3,6-dioxo-1,4-cyclohexadienyl) or tocopherol or a mimetic of superoxide dismutase or ebselen; when L is divalent decyl, divalent pentyl, or divalent propyl radical; and when B is triphenylphosphonium cation.

In one embodiment, the formulation also comprises 1 molar equivalent to 200 molar equivalents of an antioxidation agent that reduces the oxidized form of the compound of Formula 1, and a pharmaceutically acceptable carrier.

In some embodiments, the antioxidation agent is ascorbic acid.

In some embodiments, the pharmaceutically acceptable carrier comprises sorbite, glucose, and/or magnesium stearate.

In certain embodiments, the pharmaceutical formulation is SkQ1 or SkQ1H$_2$. In other embodiments, the compound is SkQR1 or SkQR1H$_2$. In yet other embodiments, the compound is SkQ3 or SkQ3H$_2$. In still other embodiments, the compound is SkQRB or SkQRBH$_2$. In other embodiments, the compound is SkQB1 or SkQB1H$_2$. In yet other embodiments, the compound is SkQBP1 or SkQBP1H$_2$.

In other aspects, the disclosure provides methods of treating and preventing diabetes type I and II, inflammation, septic shock, arthritis, and coronary heart disease, and methods of aiding in wound healing. In these methods, a therapeutically effective amount of a formulation comprising a stabilized compound of Formula I in liquid or solid form is administered to a patient, with the proviso that in compound of Formula I, A is not ubiquinone (e.g., 2-methyl-4,5-dimethoxy-3,6-dioxo-1,4-cyclohexadienyl) or tocopherol or a mimetic of superoxide dismutase or ebselen; when L is divalent decyl, divalent pentyl, or divalent propyl radical, and when B is triphenylphosphonium cation.

In some embodiments of the method, the formulation comprises glycerol, glycol, and/or ethanol. In some embodiments, the formulation comprises SkQ1, SkQ1H$_2$, SkQR1, SkQR1H$_2$, SkQ3, SkQ3H$_2$, SkQBP1, SkQBP1H$_2$, SkQRB, or SkQRBH$_2$.

In some embodiments, the liquid formulation is administered orally or by injection. In other embodiments, the solid formulation is administered orally, anally, or vaginally. In some embodiments the formulation is a solid and comprises ascorbic acid. In particular embodiments, the formulation also comprises a pharmaceutically acceptable carrier.

In some embodiments, diabetes type I or II is treated with SkQ1 or SkQ1H$_2$ in 20% glycerol.

In certain embodiments, arthritis is treated with a formulation comprising SkQ1 or SkQ1H$_2$ in 20% glycerol. In yet other embodiments, arthritis is treated with a formulation comprising SkQ1 and ascorbic acid.

BRIEF DESCRIPTION OF THE DRAWINGS

The foregoing and other objects of the present disclosure, the various features thereof, as well as the invention itself may be more fully understood from the following description, when read together with the accompanying drawings.

DESCRIPTION

Figure 1:
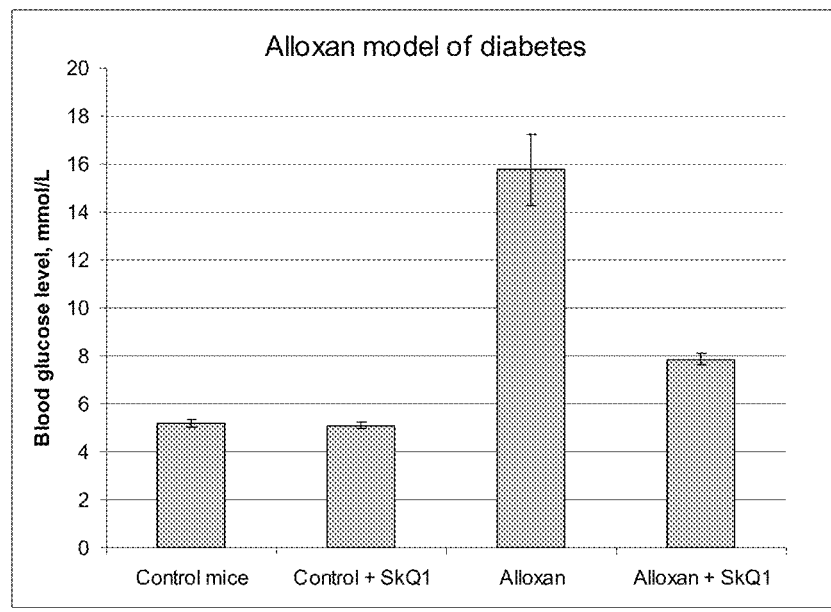
FIG. 1 is a graphic representation of the effect of SkQ1 on blood glucose level of diabetic animal model (alloxan-treated mice)

Throughout the text of a description of the invention various documents are cited. Each document cited here (including all patents, patent applications, scientific publications, specifications and manufacturer's instructions etc.), above or below, is introduced in full in this invention by reference.

Prior to the detailed description of the invention follows, one should understand that the invention is not limited to the particular methodology, protocols, and reagents described here, as they are subject to change. In addition, it should be understood that in the present invention, the terminology is used to describe particular embodiments only and does not limit the scope of the present invention which will be limited only by the appended claims. Unless otherwise specified, all technical and scientific terms used here have the same meanings that are understandable to those skilled in the art.

It was unexpectedly found that many effective MTAs are not stable enough in usual liquid and solid pharmaceutical formulations suitable for their administration by injection, or by oral, IV, nasal, topical, or enteral administration. This feature limits clinical application of pharmaceuticals based on MTA as active compounds.

I. Stabilized Formulations

The present disclosure provides stable, liquid, MTA-based pharmaceutical compositions applicable in clinical practice. A useful MTA is a compound of Formula I in oxidized and/or reduced form.

The compound of Formula I is:

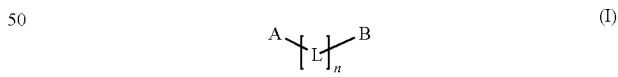
(I)

wherein:
A is an antioxidant of Formula II:

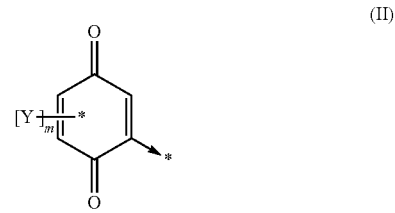
(II)

and/or reduced form thereof, wherein m comprises an integer from 1 to 3;

Y is independently selected from the group consisting of: lower alkyl, lower alkoxy, or two adjacent Y groups, together with carbon atoms to which they are attached, form a following structure of Formula III:

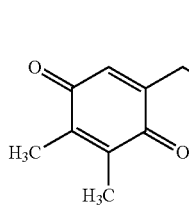

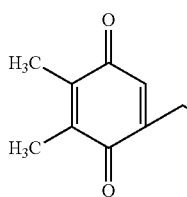

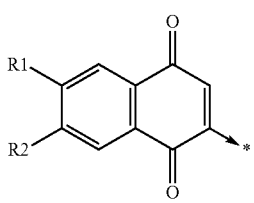
(III)

and/or reduced form thereof, wherein:

R1 and R2 are the same or different and are each independently lower alkyl or lower alkoxy;

L is a linker group, comprising: a) a straight or branched hydrocarbon chain optionally substituted by one or more double or triple bond, or ether bond, or ester bond, or C—S, or S—S, or peptide bond; and which is optionally substituted by one or more substituents preferably selected from alkyl, alkoxy, halogen, keto group, amino group; or b) a natural isoprene chain;

n is an integer from 1 to 20; and

B is a targeting group comprising: a) a Skulachev-ion Sk: (Sk$^+$ Z$^-$), wherein: Sk is a lipophillic cation or a lipophillic metalloporphyrin, and Z is a pharmaceutically acceptable anion; or b) an amphiphillic zwitterion, with the proviso that in compound of Formula I, A is not ubiquinone (e.g., 2-methyl-4,5-dimethoxy-3,6-dioxo-1,4-cyclohexadienyl) or tocopherol or a mimetic of superoxide dismutase or ebselen; when L is divalent decyl, divalent pentyl, or divalent propyl radical; and when B is triphenylphosphonium cation, with the proviso that in compound of Formula I, A is not ubiquinone (e.g., 2-methyl-4,5-dimethoxy-3,6-dioxo-1,4-cyclohexadienyl) or tocopherol or a mimetic of superoxide dismutase or ebselen; when L is divalent decyl, divalent pentyl, or divalent propyl radical; and when B is triphenylphosphonium cation.

Specific useful MTAs include, but are not limited to, the SkQ1 and SkQR1:

SkQ1

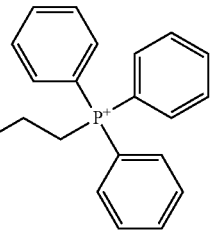

SkQR1

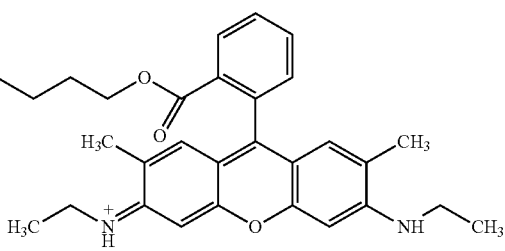

and their reduced (quinole) forms SkQ1H$_2$ and SkQR1H$_2$, respectively. These MTAs have been described in PCT/RU2006/000394.

Other useful MTA variants include, but are not limited to SkQ3:

SkQ3

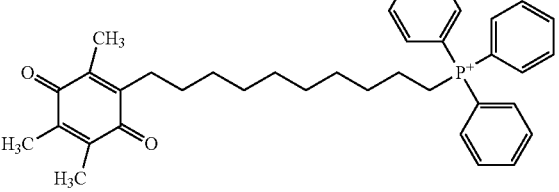

and its reduced (quinole) form SkQ3H$_2$;

to SkQRB:

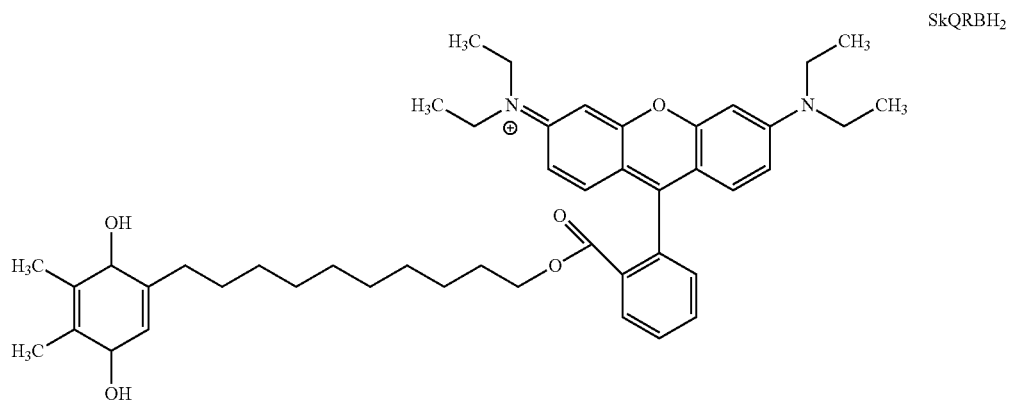 [SMILES: CCN(CC)c1ccc2c(-c3ccccc3C(=O)OCCCCCCCCCCC3=CC(O)C(C)=C(C)C3O)c3ccc(=[N+](CC)CC)cc-3oc2c1]

and its oxydized (quinone) form SkQRB;
to SkQB1:

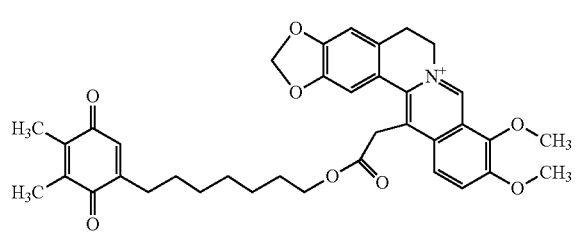

and its reduced (quinole) form, SkQB1H$_2$; and
to SkQBP1:

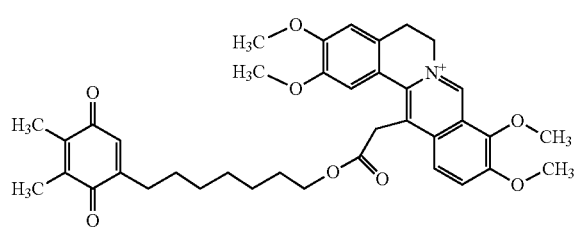

and its reduced (quinole) form SkQBP1H$_2$.

These MTAs are formulated for oral administration as liquid solutions and as solid formulations.

Liquid solutions are also useful for aerosol delivery via injection, for IV administration, nasal administration, topical administration, or enteral administration.

Such stable liquid formulations include one or more solvents or soluble components into which the MTAs are placed. Useful solvents include glycerol, ethanol, propyleneglycol, and analogous compounds. For example, useful stable formulations contain at least 10% 1,2-propylene glycol, at least 1% or at least 10% ethanol, at least 10% glycerol, or mixtures thereof, which may also include water, glycerol, ethanol, and/or 1,2-propylene to make up the difference. For example, representative stabilizing solutions of 1 nM to 1 mM SkQ1, SkQ1H$_2$, SkQR1, SkQR1H$_2$, SKQ3, SkQ3H$_2$, SKQRB, SkQRBH$_2$, SKQB1, SkQB1H$_2$, SKQBP1 and/or SkQBP1H$_2$, contain 10% to 50%, 50% to 100%, 10% to 20%, 20% to 30%, 30% to 40%, 40% to 50%, 50% to 60%, 60% to 70%, 70% to 80%, 80% to 90%, 10% to 100%, 20% to 80%, and 90% to 100% 1,2-propylene glycol, glycerol, or ethanol. Other useful percentages of such solvents include 15%, 20%, 25%, 30%, 35%, 40%, 45%, 55%, 60%, 65%, 70%, 75%, 80%, 85%, 90%, and 95%. Other pharmaceutically acceptable carriers may also be components of such formulations.

Because MTAs are not shelf-stable for long periods of time, various compounds were tested to determine their ability to stabilize SkQ1 and SkQR1 as representative MTAs in dry form.

Beta-cyclodextrin, gun-arabic, fruit fibers, and sodium chloride did not provide suitable stabilization levels (degradation rate, %/d was 0.8 to 8.1).

Liquid solvents were also tested for their ability to stabilize representative MTAs SkQ1 and SkQR1. The solvents tested were water solutions of glycerol (10% to 100%), 50% lactulose, and 1,2-propylene glycol (10% to 100%, at 60° C.). Some representative results are shown below (Table 1).

TABLE 1

| MTA | Concentration, mkM | Stabilizing Solvent | Degradation rate, percent per day |
| --- | --- | --- | --- |
| SkQ1 | 400 | 50% lactulose | 9.01 |
| SkQ1 | 400 | 10% 1,2-propylene glycol | 0.47 |
| SkQ1 | 400 | 50% 1,2-propylene glycol | 0.06 |
| SkQ1 | 400 | 100% 1,2-propylene glycol | 0.18 |
| SkQ1 | 400 | 10% Glycerol | 0.61 |
| SkQ1 | 400 | 20% Glycerol | 0.51 |
| SkQ1 | 400 | 30% Glycerol | 0.53 |
| SkQ1 | 400 | 40% Glycerol | 0.91 |
| SkQ1 | 400 | 50% Glycerol | 1.54 |
| SkQ1 | 400 | 60% Glycerol | 1.92 |
| SkQ1 | 400 | 70% Glycerol | 2.4 |
| SkQ1 | 400 | 80% Glycerol | 3.2 |
| SkQ1 | 400 | 90% Glycerol | 4.18 |
| SkQRB | 200 | 50% Glycerol | 0.4 |
| SkQR1 | 140 | 50% Glycerol | 0.7 |
| SkQBP1 | 400 | 50% Glycerol | 0.08 |
| SkQR1 | 100 | 10% 1,2-propylene glycol | 6.19 |
| SkQR1 | 100 | 20% 1,2-propylene glycol | 0.34 |
| SkQR1 | 100 | 30% 1,2-propylene glycol | 0.32 |
| SkQR1 | 100 | 40% 1,2-propylene glycol | 0.06 |
| SkQR1 | 100 | 50% 1,2-propylene glycol | <0.01 |
| SkQR1 | 100 | 60% 1,2-propylene glycol | <0.01 |

TABLE 1-continued

| MTA | Concentration, mkM | Stabilizing Solvent | Degradation rate, percent per day |
|---|---|---|---|
| SkQR1 | 100 | 70% 1,2-propylene glycol | 0.05 |
| SkQR1 | 100 | 80% 1,2-propylene glycol | 0.23 |
| SkQR1 | 100 | 90% 1,2-propylene glycol | 0.30 |
| SkQR1 | 100 | 100% 1,2-propylene glycol | 0.23 |

These results illustrate high stability of MTAs in a pharmaceutical composition for administration in the form of solution in glycerol (from about 10% to about 100% glycerol), and about 50% 1,2-propylene glycol solution.

In addition, the stability of SkQ1 and SkQR1 was significantly increased in dark plastic or glass vials, indicating that these compounds are light-sensitive. Accordingly, one of the ways to further improve or increase stability of SkQ liquid compositions during storage and transportation is to protect it from light.

When SkQ compounds of Formula I according to the disclosure are in solid form, they may be stabilized, for example, with an antioxidation agent. Such an agent can be ascorbic acid. Useful amounts of ascorbic acid range from about 1 molar equivalent to about 200 molar equivalents. As used herein, the term "molar equivalent" refers to the number of dissolved particles, or that amount which reacts with, or supplies one mole of $H^+$ in an acid-base reaction, or which reacts or supplies one mole of electrons in a redox reaction. Other useful components of representative stabilized MTA formulations are shown in Table 2. Such formulations may also comprise pharmaceutically acceptable carriers such as, but not limited to, sorbite, glucose, and magnesium stearate.

Another approach to stabilize an SkQ compound in a pharmaceutical formulation is to use its reduced (quinole) form. For example, the reduced form of SkQ1 is the quinole $SkQ1H_2$:

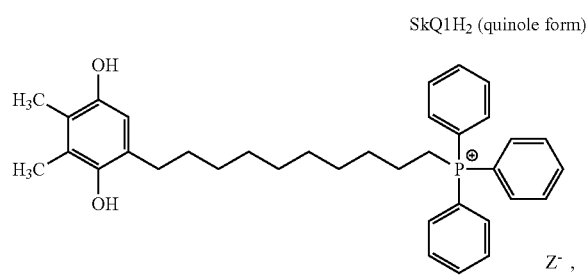 [SMILES: Cc1c(O)cc(CCCCCCCCCC[P+](c2ccccc2)(c2ccccc2)c2ccccc2)c(O)c1C]

SkQ1H$_2$ (quinole form)

where $Z^-$ is pharmaceutically acceptable anion such as, but not limited to, bromide, chloride, or ascorbate. In a dry or soluble pharmaceutical composition $SkQ1H_2$ can be stabilized and protected from oxidation by a reducing agent such as, but not limited to, ascorbate.

Yet another approach to improve stability is to place the MTA, in reduced or oxidized form, in a "softgel" formulation, which is a gelatin-based capsule with a liquid filling. Softgel formulations of MTAs provide good bioavailability as the softgel dissolves in aqueous-miscible, oily liquid carriers such as mono- and digycerides of capric/caprylic acid (Capmul MCM), Miglyol oil 8122 (medium chain triglycerides). When the softgel is released in the body, it gets emulsified and provides drug dispersion at a high surface area.

Mono- and digycerides of capric/caprylic acid (Capmul MCM), Miglyol oil 8122 (medium chain triglycerides) can be used. Such oily carriers as they become part of a self-emulsifying system. Other exemplary stabilizing components are vitamin E/polyethylene glycol succinate, sorbitan monooleate, labrasol, and combinations thereof. Additionally, based on its oxidation potential, tocopherol, butylayed hydroxytoluene, and/or butylated hydroxy anisole can be included in the composition as an antioxidant.

Another approach for increasing stabilization of MTAs in solution is to create a nanosuspension of MTA (<1000 nm) stabilized with, e.g., vitamin E/polyethylene glycol succinate. Netzsch wet milling (http://www.netzsch-grinding-.com) can be used to achieve this nanosuspension.

Additionally, ethanol solutions of reduced MTA (such as $SkQ1H_2$) can be mixed with the asorbic and acid dried to create resulting solid or powder that is stable for several months.

Stable formulations in the form of oral tablets can be prepared by hot melt extrusion. This melt granulation technique maintains the polymorphic stability of the drugs and significantly improve their oral bioavailability. It can be achieved by co-blending the MTAs with macrogols (e.g., polyethylene glycols 3350, 6000, polyvinyl pyrrolidone, hydroxy propyl cellulose and Vitamin E TPSG) through a hot melt extruder, and compressing the resulting granulation into tablets or encapsulting into hard gelatin capsules.

Representative stable liquid and solid oral SkQ1 formulations are shown below (Table 2):

TABLE 2

Oxidized SkQ1
Solutions:

SkQ1 in 20% (wt %) glycerol, prepared with phosphate buffer
SkQ1 in 50% (wt %) 1,2-propylene glycol with pyruvic acid
SkQ1 in 50% (wt %) 1,2-propylene glycol with lactic acid
Solid compositions:

SkQ1 with PEG-4000
SkQ1 with dextran
SkQ1 with p-aminobenzoic acid (p-ABA)
SkQ1 with dextran and p-ABA
SkQ1 with myoinosite
SkQ1 with pyruvic acid and Pearlitol 200
SkQ1 with pyruvic acid and microcrystalline cellulose
SkQ1 with pyruvic acid and F-Melt C
SkQ1 with pyruvic acid and Syloid FP
SkQ1 with citric (or tartaric acid, or lactic acid, or glycine) and Pearlitol 200
SkQ1 with citric acid (or tartaric acid, or lactic acid, or glycine) and crocrystalline cellulose
SkQ1 with citric acid (or tartaric acid, or lactic acid, or glycine) and F-Melt C
SkQ1 with citric acid (or tartaric acid, or lactic acid, or glycine) and Syloid FP
$SkQ1H_2$ (reduced form)
Solutions:

$SkQ1H_2$ (0.11M) with ascorbic acid (10 eq) in 55% EtOH
$SkQ1H_2$ (7.4 mM) with ascorbic acid (5 eq) and sorbite (20 wt parts) in 30% 1,2-propylene glycol
Solid compositions:

SkQ1H2 (1 eq) with ascorbic acid (>2 molar eq) with PEG-4000
SkQ1H2 (1 eq) with ascorbic acid (>2 molar eq) with dextran
SkQ1H2 (1 eq) with ascorbic acid (>10 molar eq) with PEG-4000
SkQ1H2 (1 eq) with ascorbic acid (>10 molar eq) with dextran
$SkQ1H_2$ (1 eq) with sorbite (30 wt parts)
$SkQ1H_2$ (1 eq) with ascorbic acid (0-5 eq) and sorbite (30 wt parts)

TABLE 2-continued

SkQ1H$_2$ (1 eq) with ascorbic acid (0-5 eq) and glucose (10 wt parts)
SkQ1H$_2$ (1 eq) with ascorbic acid (0-5 eq) and lactose monohydrate (10 wt parts)
SkQ1H$_2$ (1 eq) with ascorbic acid (0-5 eq) and Pearlitol 200 (30 wt parts)
SkQ1H$_2$ (1 eq) with ascorbic acid (0-5 eq) and microcrystalline cellulose (30 wt parts)
SkQ1H$_2$ (1 eq) with ascorbic acid (0-5 eq) and F-Melt C (30 wt parts)
SkQ1H$_2$ (1 eq) with ascorbic acid (0-5 eq) and Syloid FP (30 wt parts)

SkQ1H$_2$ in the from of light powder was prepared to almost a 100% yield by the reduction of SkQ1 with ascorbic acid or any other suitable reducing agent in alcohol/water mixture followed by isolation by either extraction with chloroform or any other suitable solvent, or by precipitation from water followed by centrifugal separation, or by column (silica gel) chromatography or by method HPLC RP. The isolated material was characterized by 1H NMR, LC/MC and elemental analysis data.

The sample was proved to have excellent stability for 1 month at RT or several months at 4° C. in darkness under inert atmosphere without any humidity access (Table 17). The sample also can be stabilized by being dissolved in any deoxygenated anhydrous and aprotic solvents. The reduced form of SkQ1H$_2$ quickly oxides to the original form of SkQ1 when exposed to air or wet atmosphere or dissolved in water or any protonic solvent (Table 18).

The stability of SkQ1H$_2$ in solid compositions is strongly dependent on dryness of the composition as well as dryness of excipients and other components. Humidity of ambient atmosphere and presence of air also play a crucial role in oxidation of SkQ1H$_2$ into SkQ1 followed by degradation of the latter.

II. Treatments

In vivo and in vitro experiments demonstrate the ability of MTAs including, but not limited to, SkQ1 and SkQR1, to prevent and treat diabetes and disorders related to diabetes (Example 2). Such in vivo and in vitro experiments also demonstrate that liquid solutions of MTAs, including but not limited to SkQ1 and SkQR1, can be used for prevention and treatment of inflammatory diseases and related conditions such as septic shock and/or systemic. For example, these MTA-based liquid formulations with acceptable stability combined with results showing efficacy in models of diabetes, inflammation, septic shock, and related disorders (Examples 2-7).

SkQ1 treatment also prevented disassembling of intracellular contacts and cytoskeleton reorganization caused by TNFα (data obtained by misroscopy studies of VE-cadherin, beta-cathenin and F-actin). Thus, SkQ1 was shown to be effective in protecting endothelial cells against the cytokine-caused dysfunction of endothelial barrier, and thus can be used for prevention and treatment of many pathological conditions including diabetes, atherosclerosis, aging, and chronicle inflammatory diseases.

Additionally, SkQ1 decreases the phosphorylation and degradation of IkBa caused by TNFα. NFκB is known to be permanently active in many inflammatory diseases, such as inflammatory bowel disease, arthritis, sepsis, gastritis, asthma and atherosclerosis (Monaco et al. (2004) *PNAS.*, 101:5634-9). SkQ1 was shown to prevent activation of NFκB, a key inhibitor of NFκB activity associated with elevated mortality, especially from cardiovascular diseases (Venuraju et al. (2010) *J. Am. Coll. Cardiol.*, 55:2049-61). In addition, SkQ1 was shown to prevent translocation of transcription factor p65 (RelA) from the cytoplasm to the nucleus, thereby potentially decreasing pathological consequences.

Reference will now be made to specific examples illustrating the invention. It is to be understood that the examples are provided to illustrate certain embodiments and that no limitation to the scope of the invention is intended thereby.

EXAMPLES

Example 1

Stable Formulations of Reduced Form of SkQ1 (SkQ1H$_2$)

SkQ1H$_2$, a reduced quinole form of SkQ, was prepared as follows: 10 ml SkQ1H$_2$ solution (with concentration 1 mg/ml) in ethanol was thoroughly mixed with 200 mg ascorbic acid and then vacuum dried. The resulting powder contained 95% ascorbic acid and 5% SkQ1H$_2$, and demonstrated acceptable stability at several storage temperatures. For example, in the accelerated decay experiment, SkQ1 purity was reduced from initial 98.7% to 95.1% after storage for 12 d at 60° C. From these results it can be calculated that storage for 1 year at 4° C. will result in approximately 3.5% loss from the initial concentration of the active compound SkQ1 which has acceptable stability.

Alternatively, a dry mixture of SkQ1H$_2$ and ascorbic acid is prepared by dissolving 10 mg SkQ1H$_2$ in 10 ml ascorbic acid solution (20 mg/ml) and dried under vacuum.

Yet another way to prepare an SkQ1-ascorbic acid mixture is to mix 5 ml SkQ1H$_2$ solution in ethanol (2 mg/ml), with 5 ml ascorbic acid solution in water (40 mg/ml), and vacuum dry. The reduced form of SkQH$_2$ is stabilized in ascorbic acid solution, eliminating the drying stage, and thus the corresponding liquid formulation.

Example 2

Effect of Liquid MTA Formulations on Diabetes

A. Alloxan Animal Studies

Alloxan is a well-known diabetogenic agent widely used to induce type 2 diabetes in animals (Viana et al. (2004) *BMC Pharmacol.*, 8:4-9).

Induction of the alloxan diabetes was performed as follows: Two groups of laboratory rats (20 animals in each group) with free food and water access fed a 250 nM solution of SkQ1 for 10 d. The daily rat consumption was 60 ml water solution (containing 15 nmoles SkQ1). The average weight of rats was 300 g. Thus, rats consumed approximately 50 nmol/kg body weight per day. Two other groups of animals did not receive SkQ1. After 10 d, rats were subcutaneously (in the area of the thigh) injected with alloxan dissolved in isotonic salt solution of 0.9% w/v of NaCl (100 mg/kg body weight; groups "Alloxan+SkQ1" and "Alloxan." Control animals were injected with salt solution without alloxan (groups "Control+SkQ1" and "Control"). After injection, the rats continued to drink water containing SkQ1 (250 nM) during 14 d (group "Alloxan+SkQ1") or were kept without SkQ1 (group "Alloxan").

Data on glucose blood level was measured by the glucose oxidase method (Saifer et al. (1958) *J. Lab. Clin. Med.*, 51:445-460) after 2 weeks of alloxan injection. The results are presented in FIG. 1. All data are presented as the mean+/−SE.

Animals consuming SkQ1 after alloxan injection had about 2-fold lower blood glucose compared to mice without SkQ1 treatment.

These results demonstrate that stabilized MTAs, e.g. SkQ1, are useful for the prevention and treatment of diabetes mielitus and its complications.

In another experiment, 200 g to 250 g Wistar male rats (age 7 to 8 weeks) were divided into 3 groups, 12 to 15 animals each and were injected with alloxan 125 mg/kg intraperitoneally (i.p.) after overnight fasting. Control animals were injected with saline (0.9% NaCl). The stabilized formulation (1% ethanol, 5 ml/kg) and SkQ1H$_2$ (5 eq ascorbic acid, 30 wt parts sorbite) in a dosage of 1250 nmol/kg was administered intragastrically (i.g.) by gavage once daily for 2 weeks before and 1 week after alloxan administration. Blood samples from tail vein were collected after overnight fasting and glucose levels were measured before alloxan administration and 1 d, 2 d, 3 d, and 7 d later by the conventional glucose-oxidase method. Seven days after alloxan administration rats were subjected to a glucose tolerance test. Rats were given glucose 3 g/kg i.g. Blood glucose levels were measured before glucose injection and 15 min, 30 min, 60 min, and 90 min later.

The following results were obtained (Table 3):

TABLE 3

|  | Saline + vehicle | Alloxan + vehicle | Alloxan + SkQ1H$_2$ formulation |
| --- | --- | --- | --- |
| Maximum glucose conc. in blood, mM | 6.7 | 17.6 | 13.9 |
| Integrated glucose con. in blood (area under curve, a.u = mM × min) | 500 | 1194 | 947 |

B. Diabetic Mouse Studies

Mice carrying mutation in leptin receptor gene (C57BLKS-Leprdb/J mice, or db/db mice) are known to be affected by glucose metabolic disorders. These mice are used as type II diabetes model with many of the characteristics of human disease including hyperphagia, hyperglycemia, insulin resistance, progressive obesity (Hummel et al. (1966) *Science*, 153:1127-1128).

SkQ1 in 20% glycerol, as described below in Example 8 (250 nmol/kg per day) was orally administered to 10 to 12 week old homozygous db/db mice (n=8), while vehicle db/db (n=8) and non-diabetic control heterozygous db/++ (n=5) mice for 12 weeks. The hepatic TBA-reactive substance content (MDA) was determined by assay according to the method of Mihara et al. ((1978) *Anal. Biochem.*, 86:271-278).

Figure 2:
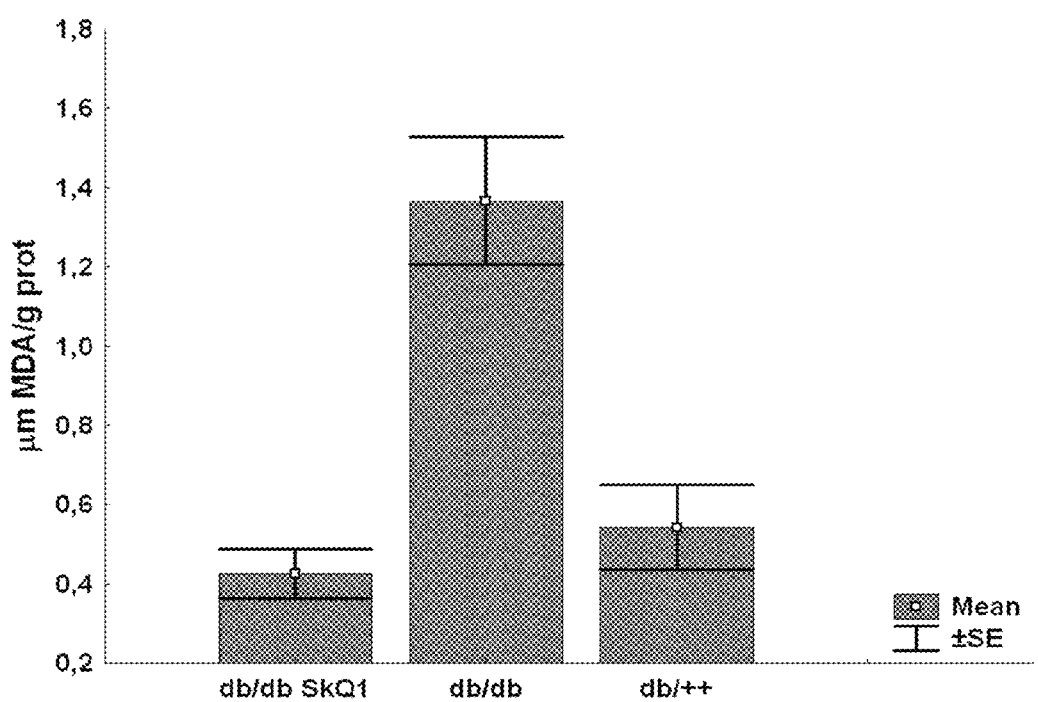
FIG. 2 is a graphic representation of the effect of SkQ1 on liver damage of db/db diabetic mice.

As shown in FIG. 2, elevated glucose levels induce oxidative stress reflected by the increased MDA levels in the liver of db/db mice. The increase of MDA level reflects stimulation of lipid peroxidation which in turn is considered responsible for the impairment of endothelial cells, capillary permeability, and fibroblast and collagen metabolism, major factors of pathologies associated with diabetes. The stabilized solution of SkQ1 significantly lowered MDA levels in the liver of diabetic db/db mice, thus indicating decreased rate of lipid peroxidation and decreased damage of the liver.

Example 3

Effect of Stabilized MTA on Wound Healing

Wound healing was studied in two series using 6 months old C57BLKS-Leprdb/J mice (db/db) homozygous and heterozygous C57BLKS-Leprdb/J mice (db/+) mice. These mice are used as type II diabetes model with impaired wound healing (Michaels, et al. (2007) *Wound Repair and Regeneration*, 15:665-670).

The mice were daily administered 250 nmol/kg body weight per day with the pharmaceutical form of SkQ1 in 20% glycerol as described in Example 8) during period of time from 10 weeks to 12 weeks. Control groups of db/db and db/+ mice were not treated with SkQ1. Full-thickness dermal wounds were made under anesthesia of ketamine (80 mg/kg). Animals were kept in plastic cages under standard temperature, light, and feeding regimes. 7 days after wounding, animals were sacrificed by decapitation. The wounds were excised, fixed in 10% formalin in standard PBS buffer, histologically processed, and embedded in paraffin. Histological sections of central part of the wounds were cut and stained with hematoxylin and eosin. The sections were immunohistochemically stained for markers of endothelial cells (CD31), macrophages (f4/80), and myofibroblasts (smooth muscle α-actin). ImageJ software (National Institutes of Health (NIH) http://rsb.info.nih.gov/ij/) was used to calculate total amount of cells, number of neutrophils, macrophages and vessel density (vessel area/granulation tissue area*100) on the microphotographs of wound sections. For each animal 100 mm$^2$ of section area was analyzed. Wound epithelization rate was assessed in % as ratio of epithelized wound area to total wound area on tissue section*100. For statistical analysis nonparametric Mann-Whitney U-test was used. Data are shown as means±S.E.M.

Figure 3A:
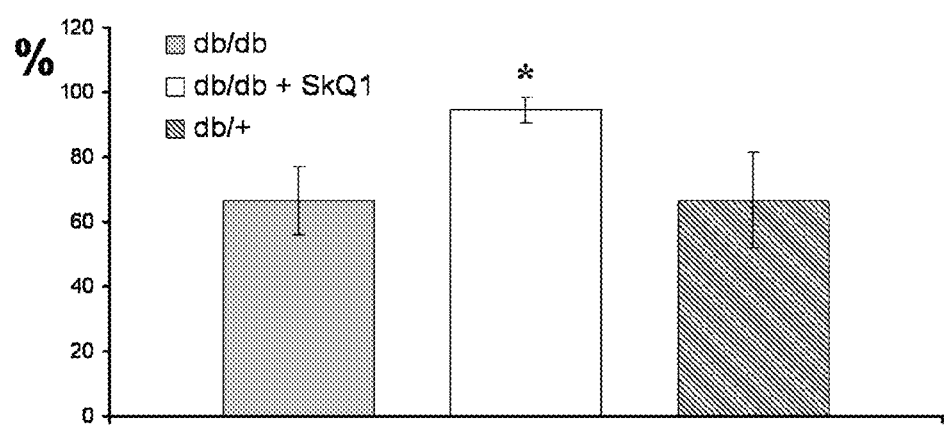
FIG. 3a is a graphic representation illustrating the effect of SkQ1 on epithelization of diabetic wounds.
Figure 3B:
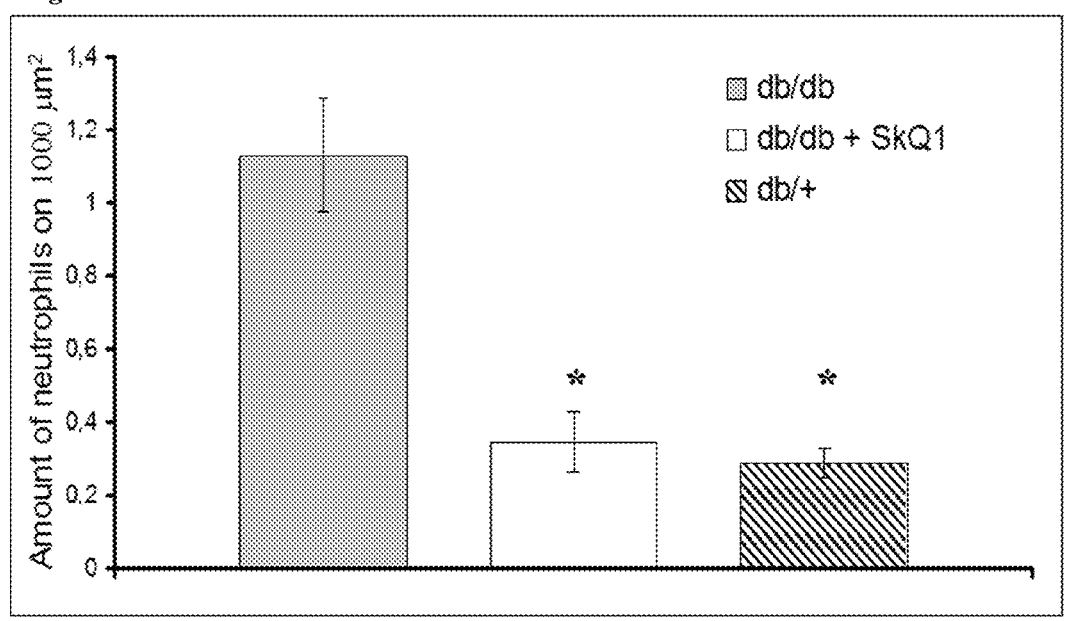
FIG. 3b is a graphic representation illustrating the effect of SkQ1 on the amount of neutrophils in diabetic wounds.
Figure 3C:
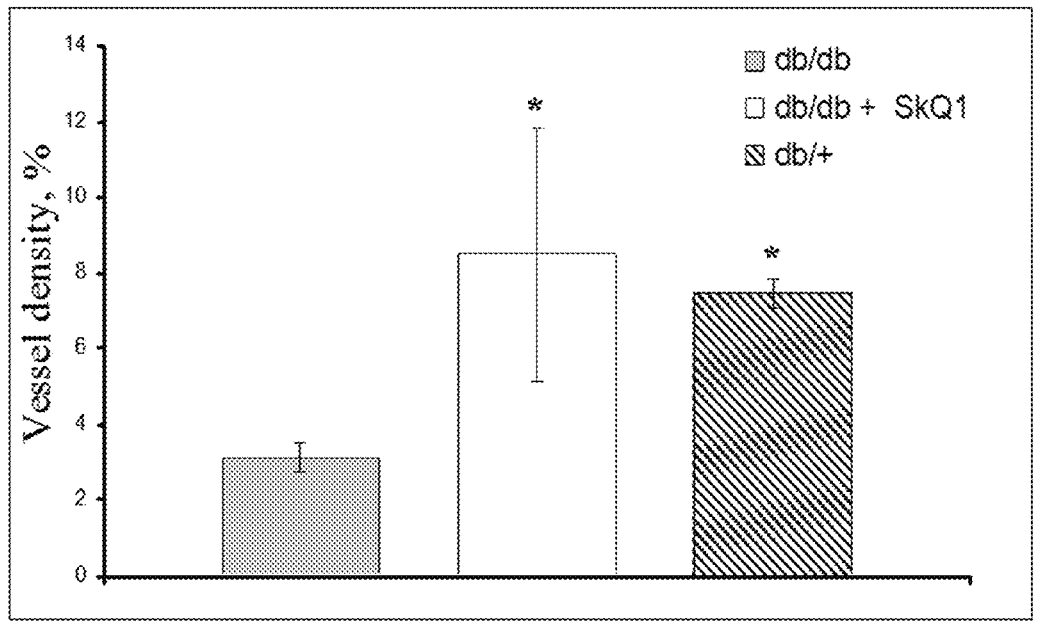
FIG. 3c is a graphic representation illustrating the effect of SkQ1 on vessel density in diabetic wounds.

As shown in FIGS. 3a, 3b and 3c, the stabilized pharmaceutical form of SkQ1 is able to accelerate wound healing by decreasing neutrophil infiltration, increasing vascularization, and increasing the rate of epithelization in diabetic mice.

Example 4

Effect of Stabilized MTA on Inflammation and Septic Shock

Septic shock is known to activate numerous inflammatory pathways in an organism leading to death. The lipopolysaccharide (LPS)-induced septic shock mouse is widely accepted model in pharmacological and biological research (Villa et al. (2004) *Meth. Molec. Med.*, 98:199-206).

Induction of the septic shock was performed as follows: 43 male BALB/c mice with free food and water access were divided onto 4 experimental groups. Group "K" got water without drugs. Groups "SkQ 50," "SkQ 250," and "SkQ 1250" were daily parenterally treated with pharmaceutical form of SkQ1 in water comprising 50 nmol/kg, 250 nmol/kg, and 1250 nmol/kg accordingly. After 3 weeks of SkQ1 treatment animals were intraperitonially injected with 250 mg/kg LPS and 700 mg/kg D-galactosamine (D-GalN) inducing septic shock leading to death of 50% of untreated control animals (LD50 dose). Death of animals were registered after 4 d of septic shock induction.

Figure 4:
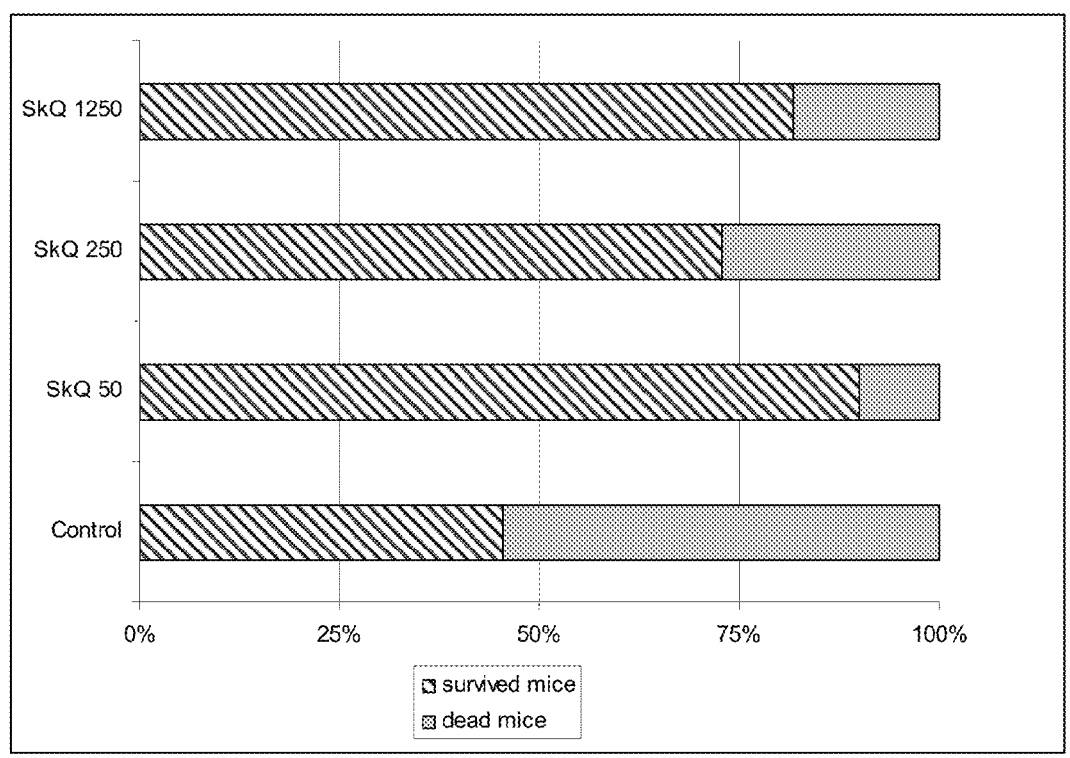
FIG. 4 is a graphic representation of the effect of SkQ1 on survival of mice subjected to septic shock.

The results of the experiment are shown on FIG. 4. The survival of mice following LPS/D-GalN treatment was significantly improved by SkQ1. The statistically significant effect was shown for a dose of 50 nmol/kg (p=0.03).

These results clearly indicate that SkQ1 acts as an anti-inflammatory agent having a therapeutic application for septic shock treatment.

In other studies, BALB/c mice with free food and water access are divided onto 4 experimental groups. Group "K" receive 20% glycerol without drugs. Groups "SkQ 50,"

"SkQ 250," and "SkQ 1250" are daily parenterally treated with pharmaceutical form of SkQ1 in 20% glycerol (Example 8) comprising 50 nmol/kg, 250 nmol/kg, and 1250 nmol/kg accordingly. After 3 weeks of SkQ1 treatment animals are intraperitonially injected with 250 mg/kg LPS and 700 mg/kg D-galactosamine (D-GalN) inducing septic shock leading to death of 50% of untreated control animals (LD50 dose). Death of the animals is registered after 4 d of septic shock induction.

Example 5

Effect of Stabilized MTA on Arthritis

The collagen-induced arthritis (CIA) rat model was used to examine the susceptibility of rheumatoid arthritis (RA) to treatment with potential anti-arthritic agents (Griffiths et al. (2001) *Immunol. Rev.*, 184:172-83).

Thirty Wistar rats with free food and water access were injected with complete Freund adjuvant and 250 mg type II collagen to induce CIA. Starting from 14 d and from 24 d after injection, two groups of 10 animals in each were daily fed with pharmaceutical form of SkQ1 in water comprising 250 nmol/kg body weight per day (groups "SkQ1 from day 14" and "SkQ1 from day 24"; Group "Control" received water without drugs).

Figure 5:
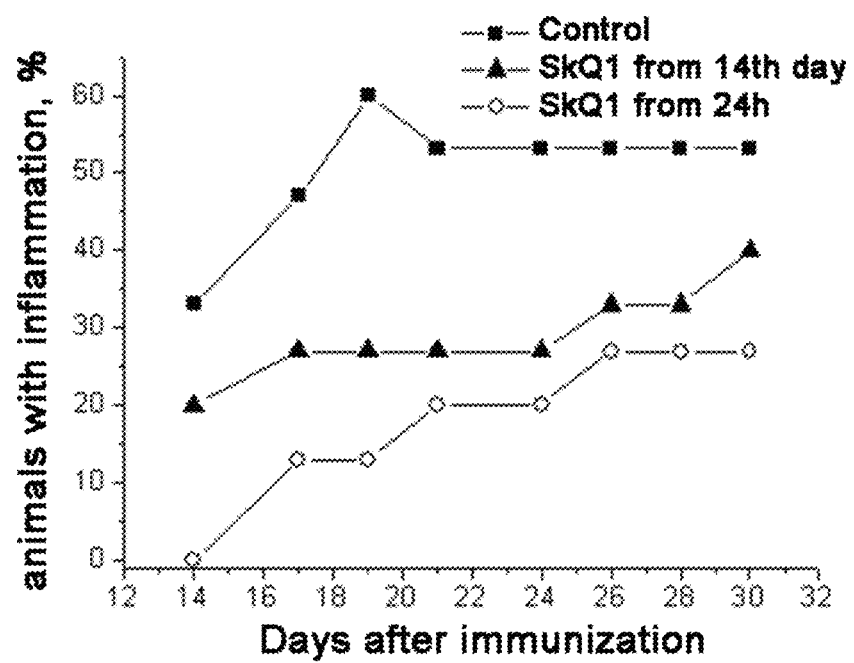
FIG. 5 is a graphic representation demonstrating the anti-inflammatory effect of SkQ1 in collagen-induced arthritis in rats.

As shown in FIG. 5, SkQ1 reduced the number of animals with apparent inflammation, i.e. animals with increased paw volumes measured by water manometry compared to control group. Hence, SkQ1 possesses anti-inflammatory and anti-arthritic effects.

In other studies, Wistar rats with free food and water access are injected with complete Freund adjuvant and 250 mg type II collagen to induce CIA. Starting from 14 d and from 24 d after injection, two groups of animals in each are daily fed with pharmaceutical form of SkQ1 in 20% glycerol (Example 8) comprising 250 nmol/kg body weight per day (groups "SkQ1 from day 14" and "SkQ1 from day 24"; Group "Control" received water without drugs).

Example 6

Effect of Stabilized MTA on Inflammation Associated with Coronary Heart Disease

Intense cytokine production induced by inflammation may lead to death of endothelial cells which, along with increased oxidative stress and vascular inflammation, leads to endothelial dysfunction and increases the risk for coronary artery disease.

Human endothelial cell line EA.hy926 (ATCC Collection; catalog number CRL-2922) was used as a model of vascular endothelium. This cell line is similar to primary HUVEC cell line (Edgell et al. (1983) *PNAS*, 80(12):3734-7; Edgell et al. (1990) *In Vitro Cell Dev Biol.*, 26(12):1167-72) and widely used as a relevant model for inflammation studies (Riesbeck et al. (1998) *Clin. Vaccine Immunol.*, 5:5675-682).

Accordingly, human endothelial cells EA.hy926 were pre-incubated with 0.2 nM SkQR1 or 2 nM SkQ1 solution in Dulbecco's Modified Eagle's Medium (DMEM) supplemented with 10% of fetal serum (Example 1) for 4 d. After that the cells were incubated overnight with fresh DMEM medium with 0.2% of fetal serum. The cells were incubated 2 d with TNF-α (0.25 ng/ml to 50 ng/ml) and cell death was monitored using standard MTT test (Berridge et al. (1996) *Biochemica*, 4:14-9). The data from this assay is shown as means±S.E. at least for 3 separate experiments.

Figure 6:
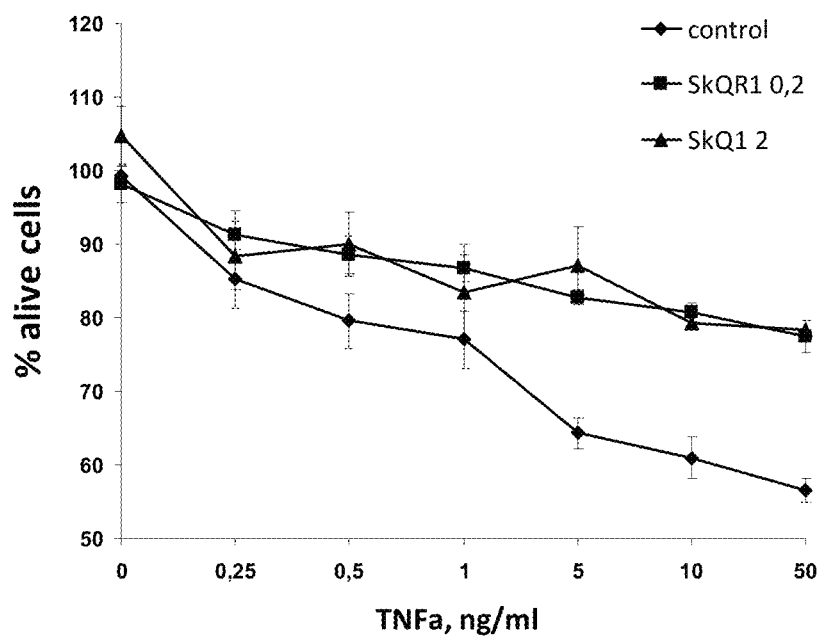
FIG. 6 is a graphic representation demonstrating the anti-inflammatory effect of SkQ1 and SkQR1 rescuing endothelial cells from death induced by proinflammatory cytokine TNF-alpha.

As shown in FIG. 6, both SkQ1 and SkQR1 greatly reduced cell death compared to control without MTA. Thus, SkQ1 and SkQR1 were shown to be effective substance protecting endothelial cells against cytokine's inflammatory action and can be used for prevention and treatment of coronary heart disease including atherothrombosis.

Example 7

Effect of Stabilized MTA on Vascular Dysfunction

A. In vitro Studies

Inflammatory cytokines induce expression of ICAM-1 (Inter-Cellular Adhesion Molecule 1). ICAM-1 is a key molecule functioning in intercellular adhesion process and transmigration of leukocytes across vascular endothelia during inflammatory response. Expression of ICAM-1, as well as inflammatory cytokines including IL-6 and IL-8, is elevated under many pathological conditions including diabetes, atherosclerosis, aging, and chronicle inflammatory diseases.

The effects of SkQ1 on ICAM-1 mRNA expression and cytokines (IL-6, IL-8) protein secretion induced by TNF-α in EAhy926 human endothelial cells (ATCC collection; catalog number CRL-2922) were examined. TNF-α is a central proinflammatory cytokine stimulating expression of cell adhesion molecules and many inflammatory cytokines. Anti-inflammatory properties of many drugs often rely on their ability to inhibit expression of pro-inflammatory cytokines induced by TNF-α using EAhy926 endothelial cells (Edgell et al. (1983) *Proc. Natl. Acad. Sci. USA*, 80:3734-7; Lombardi et al. (2009) *Eur. J. Cell. Biol.*, 88:731-42; Manea et al. (2010) *Cell Tissue Res.*, 340:71-9).

300,000 cells were plated on 60 $mm^2$ culture dishes and after attachment were treated with an SkQ1 solution (0.2 nM in DMEM medium with 10% fetal serum) for 4 d, and then stimulated with TNF-α (0.05 ng/ml for 4 h for ICAM-1 or 5 ng/ml for 15 h for cytokines, respectively). ICAM-1 mRNA expression was determined by real-time PCR (Okada et al. (2005) *Invest. Ophtalmol. Vis. Sci.*, 46:4512-8). Secretion of IL-6 and IL-8 was evaluated by ELISA (Toma et al. (2009) *Biochem. Biophys. Res. Commun.*, 390:877-82; Volanti et al. (2002) *Photochem. Photobiol.*, 75:36-45.) The data is shown as means±S.E. at least for 3 separate experiments.

Figure 7A:
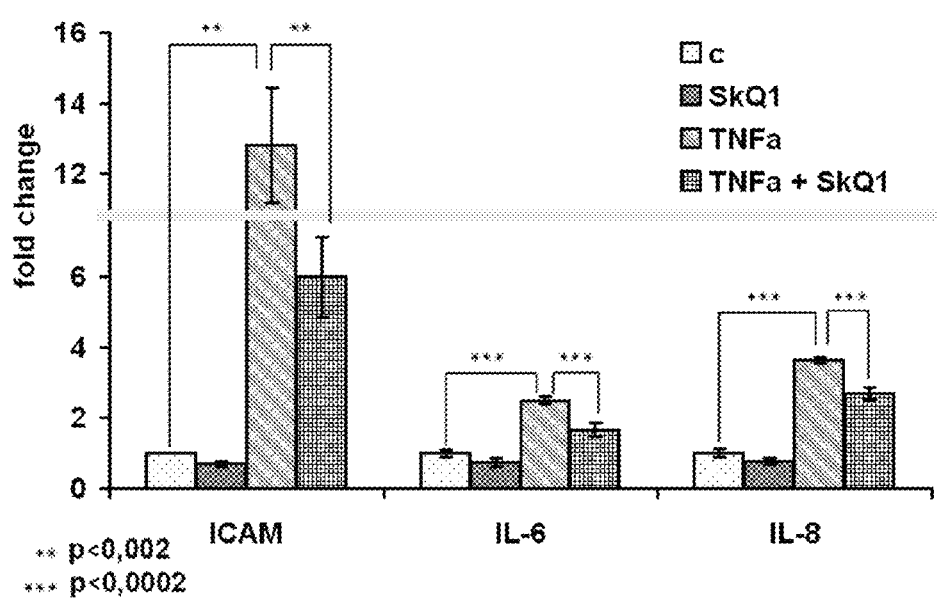
FIG. 7a is a graphic representation demonstrating the ability of SkQ1 to inhibit inflammation in vitro by lowering expression of pro-inflammatory cytokines.

The results shown in FIG. 7a confirm SkQ1 to be and effective vascular anti-inflammatory substance that prevents excessive expression of inflammatory cytokines and ICAM-1. Thus, MTAs are useful for prevention and treatment of vascular pathologies including atherosclerosis.

B. In vivo Studies

As described above in Example 7A, above, the expression of ICAM-1 is elevated under many pathological vascular conditions. SkQ1 efficacy in reducing ICAM-1 expression in vivo was tested on mice. 30 hybrid male C57Black/CBA mice were divided into 3 experimental groups (10 animals in each group) at the beginning of the experiment. The group "Young mice" included mice at the age of 6 months. Groups "Old mice" and "Old mice, SkQ1" included mice at the age of 24 months. The group "Old mice, SkQ1" had free access to drinking water with 100 nM water-dissolved SkQ1 per 1 kg of body weight for 7 months. After this period, the animals were decapitated. Aortas were excised, and total RNA was isolated using DNeasy Blood and Tissue kit (QIAGEN), reverse-transcribed into cDNA, and used for quantitative real-time PCR analysis of ICAM-1 mRNA level. For the normalization procedure the average geometry of expression levels of housekeeping genes GAPDH and RPL32 was used Data are shown as means±S.E.M.

Figure 7B:
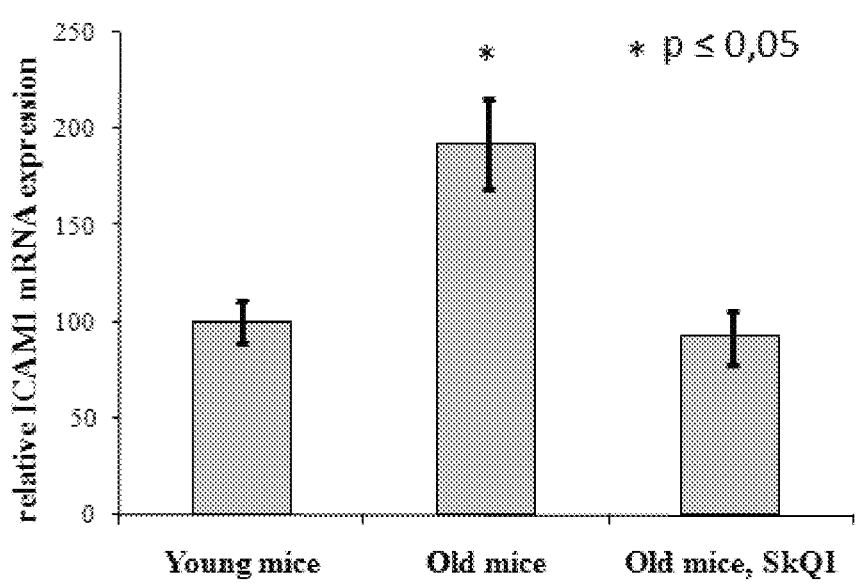
FIG. 7b is a graphic representation demonstrating the ability of SkQ1 to inhibit inflammation in vivo by lowering expression of pro-inflammatory cytokines as measured by relative ICAM-1 mRNA expression in mice.

As shown on FIG. 7b, SkQ1 significantly lowered ICAM-1 mRNA levels in treated old mice compared to the control group and approaches the level of ICAM-1 in young mice.

The results demonstrate that SkQ1 prevents the age-related increase of ICAM-1 expression in the vascular endothelium. Thus, SkQ1 can be used for prevention of age-related vascular pathologies including atherosclerosis.

In other studies, hybrid male C57Black/CBA mice are divided into 3 experimental groups, "young," "old," and "old mice, SkQ1," as described above. The third group receives SkQ1 in 20% glycerol comprising 250 nmol/kg body weight per day dose up to 7 months. The "old" group is the control and receives glycerol without drugs. After this period, the animals are decapitated. Aortas are excised, and total RNA is isolated using DNeasy Blood and Tissue kit (QIAGEN), reverse-transcribed into cDNA, and used for quantitative real-time PCR analysis of ICAM-1 mRNA level. For the normalization procedure the average geometry of expression levels of housekeeping genes GAPDH and RPL32 are used. Data are calculated as means±S.E.M.

Example 8

Preparation and Stability of Oxidized SkQ1 Formulations

1. SkQ1 in 20% (wt %) Glycerol and Phosphate Buffer

Glycerol (20 g) was diluted with phosphate buffer (80 g, 0.01 M $KH_2PO_4$, pH 4.77). A sample of SkQ1 (20 mg) was placed in a dark glass vial and dissolved in propylene glycol (0.2 mL) and diluted with an aliquot (19.8 ml) of the above solvent to 1 mM.

The stability of SkQ1 in the prepared solution was investigated by storage at RT and at 60° C. (Table 4).

TABLE 4

| Time, days | SkQ1, %/ degradation products, % (stored at RT) | SkQ1, %/ degradation products, % (stored at 60° C.) |
|---|---|---|
| 0 | 99.34/0 | 99.34/0 |
| 11 | 99.71/0 | — |
| 13 | 99.76/0 | — |
| 14 | 99.68/0 | — |
| 17 | 99.62/0 | — |
| 19 | 99.63/0.07 | 95.30/4.7 |
| 21 | 99.52/0.20 | — |
| 24 | 99.57/0.08 | — |
| 61 | 99.49/0.51 | — |

2. SkQ1 in 50% (wt %) 1,2-Propylene Glycol with Pyruvic Acid (10 Equivalents (eq) Relative to SkQ1)

SkQ1 (50 mg) and pyruvic acid (71 mg, 10 eq) were placed in a dark glass vial and dissolved in 50% propylene glycol-water mixture (100 ml) to yield a 0.081 mM SkQ1 solution.

The stability of SkQ1 in the prepared solution was investigated by storage at 60° C. (Table 5).

3. SkQ1 in 50% (wt %) 1,2-Propylene Glycol With Lactic Acid (10 eq Relative to SkQ1)

SkQ1 (50 mg) and L(+)-lactic acid (73 mg, 10 eq) were placed in a dark glass vial and dissolved in 50% propylene glycol-water mixture (100 ml) to yield a 0.081 mM SkQ1 solution.

The stability of SkQ1 in the prepared solution was investigated by storage at 60° C. (Table 5).

TABLE 5

| Time, days | SkQ1, % | SkQ1, % |
|---|---|---|
| 0 | >99.9 | >99.9 |
| 72 | 93.2 | 96.6 |

4. SkQ1 with PEG-4000

A solution of 8 mg SkQ1 in 0.5 ml EtOH was mixed with 200 mg PEG-4000, and the solvent was evaporated to dryness.

The stability of SkQ1 in the prepared composition was investigated by storage at 4° C. in darkness (Table 6).

TABLE 6

| Time, days | SkQ1, % | Degradation products, % |
|---|---|---|
| 18 | >99.9 | <0.01 |
| 19 | 99.83 | 0.17 |
| 20 | 99.80 | 0.20 |

5. SkQ1 with Dextran

A solution of 10 mg SkQ1 in 0.75 ml EtOH was added to a solution of 100 mg dextran in 1 ml water. The mixture was vigorously stirred and the solvent was evaporated to dryness.

The stability of SkQ1 in the prepared composition was investigated by storage at 60° C. in darkness (Table 7).

TABLE 7

| Time, days | SkQ1, % | Degradation products, % |
|---|---|---|
| 0 | 96.71 | 3.29 |
| 6 | 20.66 | 79.34 |
| 15 | 24.14 | 75.86 |
| 25 | 18.93 | 81.07 |

6. SkQ1 with p-aminobenzoic acid (p-ABA)

A solution of 8 mg SkQ1 in 0.5 ml EtOH was added to a solution of 200 mg p-aminobenzoic acid (p-ABA) in 1.5 ml EtOH. The solvent was evaporated to dryness.

The stability of SkQ1 in the prepared composition was investigated by storage at RT in darkness (Table 8).

TABLE 8

| Time, days | SkQ1, % | Degradation products, % |
|---|---|---|
| 0 | 100 | 0 |
| 30 | 58.42 | 41.58 |

7. SkQ1 with Dextran and p-ABA

A solution of 10 mg SkQ1 in 0.75 ml EtOH was added to a solution of p-ABA (2 mg in 0.5 ml EtOH) and dextran (100 mg in 1 ml water). The mixture was vigorously stirred and the solvent was evaporated to dryness.

The stability of SkQ1 in the prepared composition was investigated by storage at 60° C. in darkness (Table 9).

TABLE 9

| Time, days | SkQ1, % | Degradation products, % |
| --- | --- | --- |
| 0 | 97.13 | 2.87 |
| 6 | 39.22 | 60.78 |
| 15 | 7.07 | 92.93 |

8. SkQ1 (1 eq) With Myoinosite (30 wt parts relative to SkQ1)

45 mg myoinosite was added to a solution of 5 mg SkQ1 in 5 ml EtOH. The mixture was vigorously stirred and the solvent was evaporated to dryness.

The stability of SkQ1 in the prepared composition was investigated by storage at RT in darkness (Table 10).

TABLE 10

| Time, days | SkQ1, % | Degradation products, % |
| --- | --- | --- |
| 0 | 95.88 | 4.12 |
| 5 | 96.86 | 3.14 |
| 6 | 95.99 | 4.01 |
| 15 | 92.26 | 7.74 |

9. SkQ1 (1 eq) With Pyruvic Acid (10 eq) and Pearlitol 200 (30 wt parts relative to SkQ1)

375 mg Pearlitol 200 was added to a solution of 12.5 mg SkQ1 and 17.8 mg (10 eq) pyruvic acid in 0.75 ml EtOH. The mixture was vigorously stirred and the solvent was evaporated to dryness.

The stability of SkQ1 in the prepared composition was investigated by storage at 60° C. in darkness (Table 11).

10. SkQ1 (1 eq) With Pyruvic Acid (10 eq) and Microcrystalline Cellulose (30 wt parts relative to SkQ1

375 mg microcrystalline cellulose was added to a solution of 12.5 mg SkQ1 and 17.8 mg (10 eq) pyruvic acid in 0.75 ml EtOH. The mixture was vigorously stirred and the solvent was evaporated to dryness.

The stability of SkQ1 in the prepared composition was investigated by storage at 60° C. in darkness (Table 11).

11. SkQ1 (1 eq) With Pyruvic Acid (10 eq) and F-Melt C (wt parts relative to SkQ1)

375 mg F-Melt C was added to a solution of 12.5 mg SkQ1 and 17.8 mg (10 eq) pyruvic acid in 0.75 ml EtOH. The mixture was vigorously stirred and the solvent was evaporated to dryness.

The stability of SkQ1 in the prepared composition was investigated by storage at 60° C. in darkness (Table 11).

12. SkQ1 (1 eq) With Pyruvic Acid (0 eq) and Syloid FP (30 wt parts relative to SkQ1)

375 mg Syloid FP was added to a solution of 12.5 mg SkQ1 and 17.8 mg (10 eq) pyruvic acid in 0.75 ml EtOH. The mixture was vigorously stirred and the solvent was evaporated to dryness.

The stability of SkQ1 in the prepared composition was investigated by storage at 60° C. in darkness (Table 11).

TABLE 11

| Time, days | SkQ1, %/SkQ1H$_2$, %, degradation products, % | | | |
| --- | --- | --- | --- | --- |
| | (Sample 9) | (Sample 10) | (Sample 11) | (Sample 12) |
| 0 | >99.9/<0.05/<0.05 | >99.9/<0.05/<0.05 | >99.9/<0.05/<0.05 | >99.9/<0.05/<0.05 |
| 14 | 60.3/11.3/28.4 | 50.2/25.8/24.0 | 38.2/47.7/14.1 | 57.9/1.4/40.7 |

The following SkQ1 preparations can also be formulated as described supra in Example 8:

SkQ1 (1 eq) with citric (or tartaric acid, or lactic acid, or glycine, 10 eq) and Pearlitol 200 (30 wt parts in relation to SkQ1H$_2$)

SkQ1 (1 eq) with citric acid (or tartaric acid, or lactic acid, or glycine, 10 eq) and microcrystalline cellulose (30 wt parts in relation to SkQ1H$_2$)

SkQ1 (1 eq) with citric acid (or tartaric acid, or lactic acid, or glycine, 10 eq) and F-Melt C (30 wt parts in relation to SkQ1H$_2$)

SkQ1 (1 eq) with citric acid (or tartaric acid, or lactic acid, or glycine, 10 eq) and Syloid FP (30 wt parts in relation to SkQ1H$_2$)

Example 9

Preparation and Stability of Reduced SkQH$_2$ Formulations

13. SkQ1H$_2$ (1 eq) Prepared in Situ by Reduction of SkQ1 And Ascorbic Acid (2 molar eq) and PEG-4000 (10 wt parts relative to SkQ1H$_2$)

A solution of 10 mg SkQ1 in 0.6 ml EtOH was added to solution of 5.7 mg (2 eq) ascorbic acid in 0.1 ml water. The mixture was stirred until reduction to SkQ1H$_2$ completed (about 1 h). Then 100 mg PEG-4000 was added. The mixture was vigorously stirred for 30 min and the solvent evaporated to dryness.

The stability of SkQ1H$_2$ in the prepared composition was investigated by storage at 4° C. in darkness (Table 12).

14. SkQ1H$_2$ (1 eq Prepared in Situ by Reduction of SkQ1 With Ascorbic Acid (2 molar eq) and Dextran)

A solution of 10 mg SkQ1 in 0.6 ml EtOH was added to solution of 5.7 mg (2 eq) ascorbic acid in 0.1 ml water. The mixture was stirred until reduction to SkQ1H$_2$ completed (about 1 h). Then a solution of 100 mg dextran in 1 ml water was added. The mixture was vigorously stirred for 30 min and the solvent was evaporated to dryness.

The stability of SkQ1H$_2$ in the prepared composition was investigated by storage at 4° C. in darkness (Table 12).

TABLE 12

| | (Sample 13) | | | (Sample 14) | | |
| --- | --- | --- | --- | --- | --- | --- |
| Time, days | SkQ1, % | SkQ1H$_2$, % | Degradation products, % | SkQ1, % | SkQ1H$_2$, % | Degradation products, % |
| 0 | 14.65 | 85.35 | <0.05 | 3.61 | 96.39 | <0.05 |
| 1 | 7.72 | 92.28 | | 2.80 | 97.20 | |
| 4 | 59.12 | 40.88 | | 98.57 | 1.43 | |
| 6 | 57.53 | 42.47 | | 99.55 | 0.45 | |
| 7 | 54.16 | 45.84 | | 99.26 | 0.74 | |
| 10 | 54.22 | 45.78 | | 98.93 | 1.07 | |

15. SkQ1H$_2$ (1 eq) Prepared in situ by Reduction of SkQ1 With Ascorbic Acid (10 molar eq) and Dextran (10 wt parts relative to SkQ1H$_2$)

A solution of 10 mg SkQ1 in 0.6 ml EtOH was added to solution of 28.5 mg (10 eq) ascorbic acid in 0.25 ml water. The mixture was stirred until reduction to SkQ1H$_2$ was completed (about 30 min). A solution of 100 mg dextran in 1 ml water was then added. The mixture was vigorously stirred for 30 min and the solvent evaporated to dryness.

The stability of SkQ1H$_2$ in the prepared composition was investigated by storage at 60° C. in darkness (Table 13).

16. SkQ1H$_2$ (1 eq) (Prepared in situ by Reduction of SkQ1 With Ascorbic Acid (>10 molar eq) With Dextran and p-ABA (10 wt parts relative to SkQ1H$_2$ A solution of 10 mg SkQ1 in 0.6 ml EtOH was added to solution of 28.5 mg (10 eq) ascorbic acid in 0.25 ml water. The mixture was stirred until reduction to SkQ1H$_2$ was completed (about 30 min). A solution of 100 mg dextran in 1 ml water and a solution of 2 mg p-ABA in 0.5 ml EtOH were then added. The mixture was vigorously stirred for 30 min and the solvent evaporated to dryness.

The stability of SkQ1H$_2$ in the prepared composition was investigated by storage at 60° C. in darkness (Table 13).

TABLE 13

| | (Sample 15) | | | (Sample 16) | | |
|---|---|---|---|---|---|---|
| Time, days | SkQ1, % | SkQ1H$_2$, % | Degradation products, % | SkQ1, % | SkQ1H$_2$, % | Degradation products, % |
| 0 | 2.35 | 92.59 | 5.06 | 0.74 | 98.65 | 0.61 |
| 6 | 4.26 | 91.66 | 4.08 | 2.72 | 97.16 | 0.12 |
| 15 | 5.11 | 94.27 | 0.62 | 8.49 | 91.12 | 0.39 |
| 25 | 5.71 | 88.69 | 5.6 | 11.07 | 86.62 | 2.31 |

17. SkQ1H$_2$ Powder

A solution of 2 g SkQ1 in 40 ml EtOH was added to a solution of 5.7 g ascorbic acid in 60 ml water. The mixture was stirred until reduction to SkQ1H$_2$ was completed (about 30 min). Completion of reduction can be detected as the solution becomes colorless. The solvent was then evaporated off and the residue was partitioned between water (50 ml) and CHCl$_3$ (150 ml). The organic layer was washed with water (2×25 ml), dried with anhydrous sodium sulfate, filtered, and evaporated.

The yield of SkQ1H$_2$ was 2 g (approx 100% yield) in the form of light powder. The stability results are shown below (Table 14 and Table 15).

TABLE 14

| | Storage at RT | | | Storage at 60° C. | | |
|---|---|---|---|---|---|---|
| Time, days | SkQ1H$_2$, % | SkQ1, % | Degradation products, % | SkQ1H$_2$, % | SkQ1, % | Degradation products, % |
| 0 | 98.99 | 1.01 | <0.1 | 99.2 | 0.75 | 0.05 |
| 3 | 99.34 | 0.66 | <0.1 | — | — | — |
| 5 | 99.37 | 0.63 | <0.1 | 99.45 | 0.55 | 0 |
| 7 | 99.14 | 0.71 | <0.1 | 100 | 0 | 0 |
| 11 | 99.12 | 0.83 | <0.1 | 99.76 | 0.19 | 0.05 |
| 17 | 99.49 | 0.28 | <0.3 | 98.61 | 1.24 | 0.15 |
| 28 | 99.45 | 0.50 | <0.1 | 88.7 | 11.04 | 0.26 |

TABLE 15

| | 55% EtOH in water | | | CH$_2$Cl$_2$ | | |
|---|---|---|---|---|---|---|
| Time, h | SkQ1H$_2$, % | SkQ1, % | Degradation products, % | SkQ1H$_2$, % | SkQ1, % | Degradation products, % |
| 0 | 97.79 | 2.21 | 0 | 97.79 | 2.21 | 0 |
| 0.5 | 90.79 | 9.21 | 0 | 95.99 | 4.01 | 0 |
| 1.48 | 85.24 | 14.76 | 0 | 94.32 | 5.68 | 0 |
| 2.8 | 67.43 | 32.57 | 0 | 93.58 | 6.42 | 0 |
| 3.44 | 52.17 | 47.83 | 0 | 94.43 | 5.57 | 0 |
| 4.37 | 43.43 | 56.57 | 0 | 92.82 | 7.18 | 0 |
| 23.23 | 16.55 | 82.39 | 1.06 | 89.61 | 9.30 | 0.97 |
| 143.45 (~6 days) | 9.63 | 77.23 | 13.14 | 82.11 | 16.53 | 1.36 |

18. SkQ1H$_2$ (1 eq) With Sorbite (30 wt parts relative to SkQ1H$_2$)

A solution of 20 mg SkQ1H$_2$ in 1.3 ml EtOH was added to a solution of 600 mg sorbite in 1.3 ml water. The solvent was evaporated to dryness. The residue was additionally dried with diphosphorous pentoxide (P$_2$O$_5$) under reduced pressure.

The stability of SkQ1H$_2$ in the prepared composition was investigated by storage at 60° C. in darkness (Table 16).

TABLE 16

| Time, days (at 60° C.) | SkQ1H$_2$, % | SkQ1, % | Degradation products, % |
|---|---|---|---|
| 0 | 99.01 | 0.61 | 0.38 |
| 4 | 90.8 | 8.7 | 0.5 |
| 7 | 90.2 | 9.4 | 0.4 |
| 11 | 88.8 | 10.7 | 0.5 |
| 15 | 89.1 | 10.4 | 0.5 |
| 28 | 42.9 | 5.3 | 51.8 |

19. SkQ1H$_2$ (1 eq) With Ascorbic Acid (0-5 eq) and Sorbite (30 wt parts relative to SkQ1H$_2$)

Method 1:

A solution of 20 mg SkQ1H$_2$ in 1.3 ml EtOH was added to a solution of 28.4 mg (5 eq) ascorbic acid and 600 mg sorbite in 1.3 ml water. The solvent was evaporated to dryness. The residue was additionally dried with P$_2$O$_5$ under reduced pressure.

Method 2:

20 mg SkQ1H$_2$ and 28.4 mg (5 eq) ascorbic acid were added to sorbite (600 mg) melted in a glass vial (bath temperature 110° C.). slowly under vigorous stirring and stirring continued for 1 hr. The mixture was cooled to RT and vigorously triturated to provide a microcrystalline powder.

The stability of $SkQ1H_2$ in the compositions prepared by both methods was investigated by storage at 60° C. and 4° C. in darkness (Table 17).

TABLE 17

| SkQH$_2$, % | SkQ1, % | Degradation products, (total, %/number of impurities with content >0.5%) | |
|---|---|---|---|
| | | 20 days at 60° C. | 1 year at 4° C. |
| 97.753 | 1.209 | 1/0 | 0.3/0 |

Method 3:

A solution of 20 mg $SkQ1H_2$ in 1.3 ml EtOH was added to 2 mg magnesium stearate and solution of ascorbic acid (quantities as listed in the Table 18) and 600 mg glycose in 1.3 ml water (1.3 mL). The solvent was evaporated to dryness. The residue was additionally dried with $P_2O_5$ under reduced pressure.

Method 4:

20 mg $SkQ1H_2$, 2 mg magnesium stearate, ascorbic acid (quantities as listed in Table 18) and 600 mg anhydrous glycose were mixed and vigorously triturated.

The stability of $SkQ1H_2$ in compositions prepared by Methods 3 and 4 was investigated by storage at 60° C. in darkness (Table 18).

23.-25. $SkQ1H_2$ with Ascorbic Acid (0-5 eq) and Lactose Monohydrate

The compositions were prepared as described above in Method 3 or 4 using lactose monohydrate instead of glycose.

The stability of $SkQ1H_2$ in compositions prepared by both methods was investigated by storage at 60° C. in darkness (Table 18).

TABLE 18

| | Formulation (stabilizers and excipients, amounts are given in relation to SkQ1H$_2$) | | | | | Degradation products, total, %/number of impurities with content >0.5% | |
|---|---|---|---|---|---|---|---|
| Sample No | Asc. acid, eq | Glycose | L(+)-Lactose × H$_2$O | Mg Stearate | Method of preparation | 20 d at 60° C. | 1 year at 4° C. |
| 22 | 1 | ~10 wt parts | — | 10 wt % | 4 | >30/7 | ~6/2 |
| 23 | 3 | ~10 wt parts | — | 10 wt % | 4 | >12/9 | <3/1 |
| 24 | 0.3 | ~10 wt parts | — | 10 wt % | 4 | >9/7 | <3/1 |
| 25 | 1 | — | ~10 wt parts | 10 wt % | 4 | >12/7 | 4.6/1 |
| 26 | 3 | — | ~10 wt parts | 10 wt % | 4 | >9/6 | <3/2 |
| 27 | 0.3 | — | ~10 wt parts | 10 wt % | 4 | >10/5 | 3.9/2 |
| 28 | 1 | ~10 wt parts | — | 10 wt % | 3 | ~6/3 | 2.8/0 |
| 29 | 2 | ~10 wt parts | — | 10 wt % | 3 | 4.4/1 | 2.6/0 |
| 30 | 3 | ~10 wt parts | — | 10 wt % | 3 | 4.2/0 | 2/0 |
| 31 | 5 | ~10 wt parts | — | 10 wt % | 3 | 3.6/0 | 1.6/0 |
| 32 | 0.3 | ~10 wt parts | — | 10 wt % | 3 | 3.5/3 (7 d at 60° C.) | — |

The following $SkQ1H_2$ preparations in ascorbic acid are also prepared as in Example 19 supra:

$SkQ1H_2$ (1 eq) with ascorbic acid (0-5 eq) with magnesium stearate (10 wt % in relation to $SkQ1H_2$) and glucose (10 wt parts in relation to $SkQ1H_2$)

$SkQ1H_2$ (1 eq) with ascorbic acid (0-5 eq) with magnesium stearate (10 wt % in relation to $SkQ1H_2$) and lactose monohydrate (10 wt parts in relation to $SkQ1H_2$)

$SkQ1H_2$ (1 eq) with ascorbic acid (0-5 eq) and Pearlitol 200 (30 wt parts in relation to $SkQ1H_2$)

$SkQ1H_2$ (1 eq) with ascorbic acid (0-5 eq) and microcrystalline cellulose (30 wt parts in relation to $SkQ1H_2$)

$SkQ1H_2$ (1 eq) with ascorbic acid (0-5 eq) and F-Melt C (30 wt parts in relation to $SkQ1H_2$)

$SkQ1H_2$ (1 eq) with ascorbic acid (0-5 eq) and Syloid FP (30 wt parts in relation to $SkQ1H_2$)

20-22 and 26-30. $SkQ1H_2$ With Ascorbic Acid (0-5 eq) and Glucose

31. $SkQ1H_2$ with Ascorbic Acid in 55% EtOH

A solution of pure $SkQ1H_2$ (1 g in 5 ml EtOH) was added to solution of ascorbic acid (2.85 g (10 eq) in 10 ml water).

The stability of $SkQ1H_2$ in the prepared solution was investigated by storage at RT in darkness (Table 19).

TABLE 19

| Time, h | SkQ1H$_2$, % | SkQ1, % | Degradation products, % |
|---|---|---|---|
| 0 | 99.73 | 0.27 | <0.01 |
| 1.5 | 99.07 | 0.93 | <0.01 |
| 68 (~3 days) | 99.05 | 0.59 | <0.4 |
| 118 (~5 days) | 99.69 | 0.31 | <0.01 |
| 165 (~7 days) | 99.74 | 0.26 | <0.01 |

32. $SkQ1H_2$ with Ascorbic Acid and Sorbite in 30% 1,2-Propylene Glycol

A solution of pure $SkQ1H_2$ (50 mg in 1 ml 1,2-propylene glycol) was added to solution of ascorbic acid (67.4 mg (5 eq)) and sorbite (1.5 g) in 10 ml water.

The stability of $SkQ1H_2$ in the prepared solution was investigated by storage at 60° C. in darkness (Table 20).

TABLE 20

| Time, days | SkQ1, % | SkQH$_2$, % | Degradation products, % |
|---|---|---|---|
| 0 | 0.18 | 99.82 | 0.00 |
| 3 | 1.03 | 98.67 | 0.30 |
| 14 | 28.34 | 69.51 | 2.15 |
| 27 | 51.9 | 3.2 | 44.9 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of treating dermal wounds, comprising orally administering to a patient in need thereof a therapeutically effective amount of a formulation comprising a compound of Formula I, in liquid or solid form:

(I)

wherein:
A is an antioxidant having the structure of Formula II:

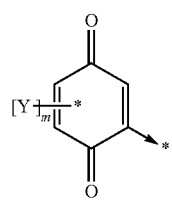
(II)

and/or reduced form thereof, wherein:
m comprises an integer from 1 to 3;
Y is methyl;
L is a linker group, comprising a straight or branched hydrocarbon chain optionally substituted by one or more double or triple bond, or ether bond, or ester bond, or C—S, or S—S, or peptide bond; and which is optionally substituted by one or more substituents selected from alkyl, alkoxy, halogen, keto group, amino group;
n is an integer from 1 to 20; and
B is a targeting group, and is:
a Skulachev ion Sk$^+$Z$^-$, wherein:
Sk is a lipophilic cation or a lipophilic metalloporphyrin; and
Z is a pharmaceutically acceptable anion,
the compound being stabilized in about 10% to about 100% of a liquid solvent selected from the group consisting of propylene glycol and glycerol.

2. A method of treating an inflammatory disorder, comprising orally administering to a patient in need thereof a therapeutically effective amount of formulation comprising a stabilized compound of Formula I in liquid or solid form:

(I)

wherein:
A is an antioxidant having the structure of Formula II:

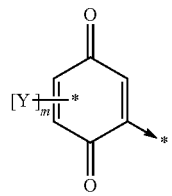
(II)

and/or reduced form thereof, wherein:
m comprises an integer from 1 to 3;
Y is methyl;
L is a linker group, comprising a straight or branched hydrocarbon chain optionally substituted by one or more double or triple bond, or ether bond, or ester bond, or C—S, or S—S, or peptide bond; and which is optionally substituted by one or more substituents selected from alkyl, alkoxy, halogen, keto group, amino group;
n is an integer from 1 to 20; and
B is a targeting group, and is:
a Skulachev ion Sk$^+$Z$^-$, wherein:
Sk is a lipophilic cation or a lipophilic metalloporphyrin; and
Z is a pharmaceutically acceptable anion,
the compound being stabilized in about 10% to about 100% of a liquid solvent selected from the group consisting of propylene glycol and glycerol.

3. The method of claim 2, wherein the inflammatory disorder is arthritis.

4. The method of claim 2, wherein the formulation comprises SkQ1 in 20% glycerol.

5. A pharmaceutical formulation comprising a compound of Formula I in oxidized and/or reduced form in a light-protected vial, the compound of Formula I being:

(I)

wherein:
A is an antioxidant having the structure of Formula II:

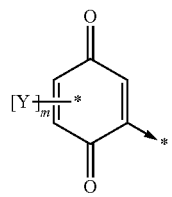
(II)

and/or reduced form thereof, wherein:
m comprises an integer from 1 to 3;
Y is methyl;
L is a linker group comprising a straight or branched hydrocarbon chain optionally substituted by one or more double or triple bond, or ether bond, or ester bond, or C—S, or S—S, or peptide bond; and which is optionally substituted by one or more substituents selected from alkyl, alkoxy, halogen, keto group, amino group;

n is an integer from 1 to 20; and

B is a targeting group, and is:
  a Skulachev ion Sk⁺Z⁻, wherein:
    Sk is a lipophilic cation or a lipophilic metalloporphyrin; and
    Z is a pharmaceutically acceptable anion,
the compound being stabilized in about 10% to about 100% of a liquid solvent selected from the group consisting of propylene glycol and glycerol.

6. The pharmaceutical formulation of claim 5, wherein the light-protected vial comprises dark plastic or glass.

7. A pharmaceutical formulation comprising a compound of Formula I in oxidized or reduced form:

(I)

wherein:

A is an antioxidant having the structure of Formula II:

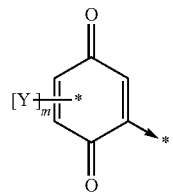
(II)

and/or reduced form thereof, wherein:

m comprises an integer from 1 to 3;

Y is methyl;

L is a linker group comprising a straight or branched hydrocarbon chain optionally substituted by one or more double or triple bond, or ether bond, or ester bond, or C—S, or S—S, or peptide bond; and which is optionally substituted by one or more substituents selected from alkyl, alkoxy, halogen, keto group, amino group;

n is an integer from 1 to 20; and

B is a targeting group, and is:
  a Skulachev ion Sk⁺Z⁻, wherein:
    Sk is a lipophilic cation or a lipophilic metalloporphyrin; and
    Z is a pharmaceutically acceptable anion,
the compound being stabilized in about 10% to about 100% of a liquid solvent selected from the group consisting of propylene glycol and glycerol.

8. The pharmaceutical formulation of claim 7, wherein the compound of Formula I is SkQ1.

9. The pharmaceutical formulation of claim 7, wherein the weight % of propylene glycol in the pharmaceutical formulation is about 50%.

* * * * *